(12) United States Patent
Richter Dahlfors et al.

(10) Patent No.: US 9,958,439 B2
(45) Date of Patent: May 1, 2018

(54) CARBOHYDRATE DETECTION

(71) Applicant: RICHTER LIFE SCIENCE DEVELOPMENT AB, Saltsjö-Boo (SE)

(72) Inventors: Agneta Richter Dahlfors, Saltsjö-Boo (SE); Xiankeng Choong, Hägersten (SE)

(73) Assignee: RICHTER LIFE SCIENCE DEVELOPMENT AB, Saltsjö-Boo (SE)

(*) Notice: Subject to any disclaimer, the term of this patent is extended or adjusted under 35 U.S.C. 154(b) by 290 days.

(21) Appl. No.: 14/408,440

(22) PCT Filed: Jun. 27, 2013

(86) PCT No.: PCT/SE2013/050810
§ 371 (c)(1),
(2) Date: Dec. 16, 2014

(87) PCT Pub. No.: WO2014/007730
PCT Pub. Date: Jan. 9, 2014

(65) Prior Publication Data
US 2015/0212076 A1   Jul. 30, 2015

(30) Foreign Application Priority Data

Jul. 2, 2012 (SE) .................................. 1250751

(51) Int. Cl.
G01N 33/52 (2006.01)
G01N 33/53 (2006.01)
(Continued)

(52) U.S. Cl.
CPC ....... *G01N 33/5308* (2013.01); *C07D 333/24* (2013.01); *C07D 409/14* (2013.01);
(Continued)

(58) Field of Classification Search
CPC .................. G01N 33/5308; G01N 33/52
See application file for complete search history.

(56) References Cited

FOREIGN PATENT DOCUMENTS

WO   WO-2005/045065 A1   5/2005
WO   WO-2007/075595 A2   7/2007
(Continued)

OTHER PUBLICATIONS

Lan et al., "Copolythiophene-Derived Colorimetric and Fluorometric Sensor for Visually Supersensitive Determination of Lipopolysaccharide" J. Am. Chem. Soc., vol. 134, pp. 6685-6694, published Mar. 27, 2012.*

(Continued)

*Primary Examiner* — Tracy Vivlemore
*Assistant Examiner* — Nam P Nguyen
(74) *Attorney, Agent, or Firm* — Harness, Dickey and Pierce, P.L.C.

(57) ABSTRACT

The present invention relates to a method for detection, identification and/or quantification of one or more carbohydrates. The method comprises the steps of contacting an objector a sample with a luminescent conjugated oligothiophene (LCO) and detecting at least one detection signal of the luminescent conjugated oligothiophene. The presence of and/or the identity of and/or the quantity of one or more carbohydrates that is or are present on said object or in said sample is determined based on said detected detection signal from the LCO. The invention encompasses methods for carbohydrate detection by use of oligothiophene derivatives. The methods are quick, easy and direct and can be performed in real time as well as in situ.

18 Claims, 29 Drawing Sheets

(51) Int. Cl.
| C07D 333/24 | (2006.01) |
| C07D 409/14 | (2006.01) |
| G01N 33/50 | (2006.01) |
| G01N 33/58 | (2006.01) |
| G01N 33/68 | (2006.01) |

(52) U.S. Cl.
CPC ............ *G01N 33/50* (2013.01); *G01N 33/52* (2013.01); *G01N 33/582* (2013.01); *G01N 33/68* (2013.01); *G01N 2400/00* (2013.01); *G01N 2400/12* (2013.01); *G01N 2400/40* (2013.01)

(56) References Cited

FOREIGN PATENT DOCUMENTS

| WO | WO-2010/044744 A1 | 4/2010 |
| WO | WO-2011/102789 A1 | 8/2011 |
| WO | WO-2012/072980 A1 | 6/2012 |

OTHER PUBLICATIONS

Merriam-Webster.com, print retrieved Jun. 11, 2017, print retrieved from <https://www.merriam-webster.com/dictionary/oligo>.*

Rosen et al., "Biosynthesis of Bacterial lipopolysaccharide", Journal of Biological Chemistry, vol. 239, No. 10, pp. 3196-3200 Oct. 1964.*

Schmid et al., "Self-Assembling Carbohydrate-Functionalized Oligothiophenes", Organic Letters, vol. 11, No. 22, pp. 5098-5101, published Oct. 21, 2009.*

Hu et al., "D-Mannose: Properties, Production, and Applications: An Overview", Comprehensive Reviews in Food Science and Food Safety, vol. 15, pp. 773-785, published 2016.*

Navarre et al., "Surface Proteins of Gram-Positive Bacteria and Mechanisms of Their Targeting to the Cell Wall Envelope", Microbiol. Mol. Bio. Reviews, p. 174-229, Mar. 1999.*

Lee et al., "A lipopolysaccharide- and B-1,3-Glucan-binding Protein from Hemocytes of the Freshwater Crayfish *Pacifastacus leniusculus*", Journal of Biological Chemistry, vol. 275, No. 2, pp. 1337-1343, published Jan. 14, 2000.*

Åslund, A., et al. (2009), "Novel Pentameric Thiophene Derivatives for in Vitro and in Vivo Optical Imaging of a Plethora of Protein Aggregates in Cerebral Amyloidoses", *ACS Chemical Biology*, 4(8): 673-684.

Åslund, A., et al. (2007), "Studies of Luminescent Conjugated Polythiophene Derivatives: Enhanced Spectral Discrimination of Protein Conformational States", *Bioconjugate Chem*, 18: 1860-1868.

Klingstedt, T., et al. (2011), "Synthesis of a library of oligothiophenes and their utilization as fluorescent ligands for spectral assignment of protein aggregates", *Organic & Biomolecular Chemistry*, 9: 8356-8370.

Klingstedt, T., et al. (2011), "Conjugated polymers for enhanced bioimaging", *Biochimica et Biophysica Acta*, 1810: 286-296.

Žídková, J., et al. (2001), "Determination of saccharides in fruit juices by capillary electrophoresis and matrix-assisted laser desorption/ionization time-of-flight mass spectrometry", *Journal of Mass Spectrometry*, 36: 417-421.

International Search Report dated Oct. 16, 2013 issued in PCT application No. PCT/SE2013/050810.

Harvey, David J., "Analysis of Carbohydrates and Glycoconjugates by Matrix-Assisted Laser Desorption/Ionization Mass Spectrometry: an Update for 2007-2008.", Mass Spectrometry Reviews Mar.-Apr. 2012, vol. 31, No. 2, pp. 183-311 (2012).

Nilsson et al., "A Pentameric Luminescent-Conjugated Oligothiophene for Optical Imaging of in Vitro-Formed Amyloid Fibrils and Protein Aggregates in Tissue Sections.", Database Medline [Online] US National Library of Medicine (NLM), Bethesda, MD (2012).

Supplemental European Search Report dated Mar. 2, 2016 issued in PCT application No. PCT/SE2013/050810.

* cited by examiner

A

B

C

D

CARBOHYDRATE DETECTION

PRIORITY STATEMENT

This application is a national stage application under 35 U.S.C. § 371 of PCT International Application No. PCT/SE2013/050810 which has an international filing date of 27 Jun. 2013 and claims priority under 35 U.S.C. § 119 to Sweden Application No. 1250751-3 filed 2 Jul. 2012. The contents of each application recited above are incorporated herein by reference in their entirety.

FIELD OF THE INVENTION

The present invention relates to the use of luminescent conjugated oligothiophenes (LCOs) for detection of carbohydrates and monitoring of carbohydrate formation or carbohydrate conversion.

BACKGROUND OF THE INVENTION

Carbohydrates are often polymeric and are named, grouped and classed according to the identity of the composed monosaccharide, the number of monomeric units, and the carbon position of the covalent bonds linking each monosaccharide.

Currently a wide range of methods for detection, identification and quantification of carbohydrates are known and applied across all industries. However, few of these methods have sufficient resolution to identify the precise molecule. This is due to the inherent nature of the chemical structure of polysaccharides, which are large macromolecules composed of a small group of identical subunits. As a result of this repetitive nature, carbohydrates do not commonly present unique epitopes or binding surfaces for easy detection with probes. The lack of unique epitopes and difficulty of detection is in contrast to proteins, which have several levels of structural conformations and unique qualities in addition to the primary amino acid sequence. In contrast to proteins, antibody based detection systems are rarely effective when used for carbohydrates.

Identification of carbohydrates is commonly performed by indirect means and is biased towards soluble carbohydrates. For example, the carbohydrate identity may be uncovered by an initial monomerization step, followed by an identification step in which each monomer and the percentage of each monomer present is identified. The gained monomer information is then fed back into a determination step in which the identity of the original carbohydrate is determined.

Other common techniques for carbohydrate analysis use a combination of chromatography (e.g. thin layer chromatography, gas chromatography, high performance liquid chromatography) and detailed chemical analysis by electrophoresis or mass spectrometry of polymers or monomers. Often, mass spectrometry is used in combination with a prior step of separation to purify a mixture before analysis. In addition, monomerization of the polysaccharide chain is often a requirement for analysis of larger carbohydrates. While highly accurate, the singular and/or sequential use of the above methods can be slow and cumbersome, and requires a significant amount of expertise (Zidková J and Chmelík J, J. Mass Spectrom. (2001), 36(4):417-21).

In nature, carbohydrates are as ubiquitous as proteins. They function both as substrates in metabolism, as structural macromolecules, and as ligands/targets for adhesion, signaling and in many biological interactions. In pharmaceutical industries as well as other industrial settings, carbohydrates represent several high grossing products in the market. These products range from drugs to foods and supplements to new polymers for 'green' materials. A simple sensitive method for carbohydrate identification and quantification is anticipated to be of great usefulness in these settings.

WO2010/044744 A1 discloses novel thiophene compounds for use in in vivo imaging of amyloid or aggregated forms of proteins. The document discloses randomly polymerized polythiophenes, as well as oligomeric thiophenes of defined length, that bind to and enable detection of such proteins. The disclosed oligothiophene compounds are for example useful for diagnosis of Alzheimer's disease and other diseases involving aggregated or misfolded proteins.

Åslund, A et al (ACS Chem. Biol. (2009), 4(8):673-684) discloses pentameric luminescent conjugated oligothiophenes for selective identification of protein aggregates. The disclosed LCOs can be utilized as research tools for studying protein aggregation diseases such as prionic diseases and Alzheimer's disease.

Klingstedt, T et al (Org. Biomol. Chem. (2011), 9:8356-8370) discloses a library of luminescent conjugated oligothiophenes of different lengths as well as their method of synthesis. The disclosed luminescent conjugated oligothiophenes are useful for selective identification of protein aggregates, They facilitate the study of protein aggregation diseases and could also be utilized for the development of novel diagnostic tools for such diseases.

SUMMARY OF THE INVENTION

It is a general object of the present invention to provide molecular probes, and methods utilizing such molecular probes, that can be used for carbohydrate detection and analysis. It is another object of the invention to provide probes and methods which can discriminate between different carbohydrates. Areas of analysis include quantification, purity determination and tracking of synthesis rate and efficiency. An encompassing object to this is to provide probes for in vitro, in vivo and in situ detection and analysis of biologically relevant carbohydrates. Yet another object of the invention is to provide probes and methods to follow carbohydrate synthesis, verification and analysis of end product/substrate identity and purity analysis.

These objects are achieved by a molecular probe and a method according to the appended claims.

The invention relates to the use of a luminescent conjugated oligothiophene for detection, identification and/or quantification of one or more carbohydrates.

In one aspect of the invention there is provided a method for detection, identification and/or quantification of one or more carbohydrates, comprising the steps of:
  contacting an object or a sample with a luminescent conjugated oligothiophene;
  detecting at least one detection signal of the luminescent conjugated oligothiophene; and
  based on said detected detection signal determining the presence, identity and/or quantity of the carbohydrate or carbohydrates on said object or in said sample.

The luminescent conjugated oligothiophene (LCO) may be a pentameric to 15-meric luminescent conjugated oligothiophene. Preferably, the luminescent conjugated oligothiophene is a pentameric or heptameric luminescent conjugated oligothiophene. In one embodiment the luminescent conjugated oligothiophene comprises one or more functional side chains, such as amino acids, amino acid derivatives, neurotransmitters, monosaccharides, polysaccharides, nucleic acids and derivatives as well as combinations thereof. Disclosed herein are the example heptameric luminescent conjugated oligothiophenes h-FTAA and h-HTAA, and the example pentameric luminescent conjugated oligothiophenes p-HTA-Lys, p-HTEA, p-HTIm, p-HTA-Tyr, p-HTA-Arg, p-HTA-Asp and p-HTA-Glu.

In one embodiment the detection signal is an optical signal, such as a fluorescence signal or a colorimetric signal, or an electrical signal such as conductivity.

In an advantageous embodiment the luminescent conjugated oligothiophene is able to discriminate between at least two different carbohydrates, enabling identification and/or quantification of different carbohydrates on the object or in the sample.

The luminescent conjugated oligothiophene may target at least one insoluble carbohydrate, such as cellulose, chitin, β-glucan, alginate, amylose and glycogen, or combinations thereof.

Alternatively or additionally, the luminescent conjugated oligothiophene may target at least one soluble carbohydrate, such as glucose, cellulobiose, heparin, chondroitin sulfate A, or combinations thereof.

The contacting and/or detecting steps may be carried out in vivo or in situ.

In one aspect of the invention there is provided novel luminescent conjugated oligothiophene compounds selected from pHTA-Tyr, pHTA-Arg, pHTA-Asp, pHTA-Glu and pHTA-Lys. The compounds are all useful in methods according to the present disclosure.

BRIEF DESCRIPTION OF THE FIGURES

The invention is now described, by way of example, with reference to the accompanying figures, in which.

DETAILED DESCRIPTION

Figure 1A:
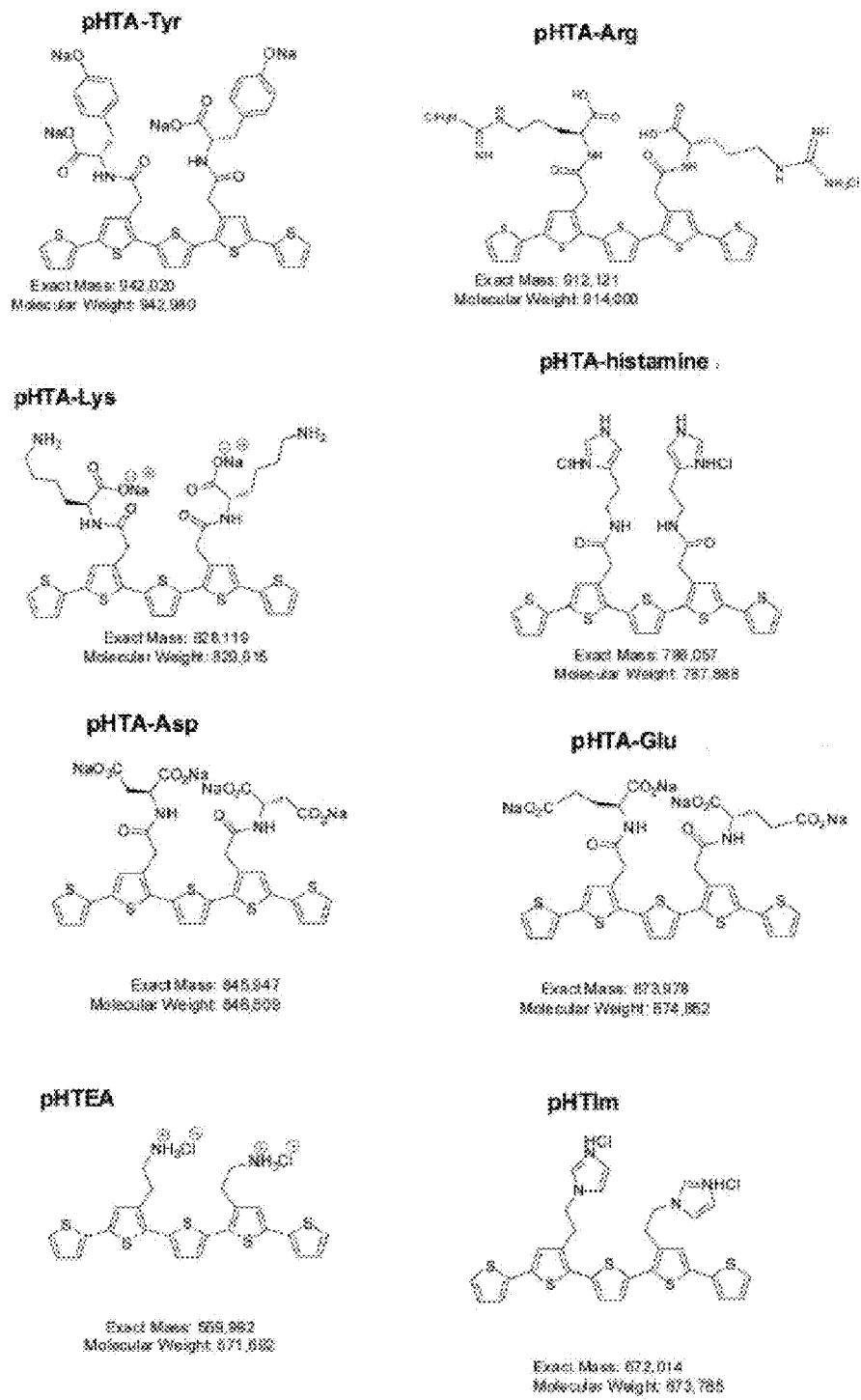
FIG. 1 shows A) exemplifying embodiments of pentameric luminescent conjugated oligothiophenes (LCOs) of the present disclosure, and B) exemplifying embodiments of heptameric luminescent conjugated oligothiophenes (LCOs) of the present disclosure.

The present invention relates to molecular probes, so called luminescent conjugated oligothiophenes (LCOs) for use in carbohydrate detection, identification and analysis.

A particular LCO probe targets and binds to one or several different carbohydrates, as exemplified by the prototype probes in this disclosure. When the LCO is exposed to and interacts with a target carbohydrate, the LCO molecule undergoes a unique geometric change, which is reflected by a target specific output signal that can be detected as a detection signal. The output signal may for instance be detected as a spectrofluorometric signal, a colorimetric signal, a change in electrical conductivity, or a combination of different signals. The geometric change may for instance result in an increased or decreased emitted fluorescence signal and/or in a shift in excitation wavelength for peak emission ($\lambda$max). In one alternative, the geometric change may result in a measurable change in conductivity of the LCO or a conductive polymer coupled thereto.

Profiling of individual target specific detection signals of an LCO, which are produced with each binding target, allows for identification and quantification of specific carbohydrates. Many of the prototype LCOs in this disclosure have dual or multiple sensitivity for different carbohydrates and are able to discriminate between them by yielding detection signals that are specific for each target carbohydrate.

Analysis of LCO detection signals in this disclosure is comprised largely of spectrofluorometric readouts, to which the excitation wavelength for peak emission ($\lambda$max) as well as the intensity of emitted fluorescence are of particular interest. Included are the excitation and emission spectra of target bound LCOs. The excitation spectrum entails the detection of the intensity of fluorescence emitted at a specific wavelength when the LCO in a sample is excited by lasers within a range of wavelengths. The emission spectrum entails the detection of the intensity of emissions at different wavelengths within a specified range, when LCOs within a sample are excited at a defined wavelength.

Prototype LCOs in this disclosure show sensitivity to carbohydrates in a biologically relevant detection range. This includes structural carbohydrates (eg. β-1,3-glucan, cellulose, chitin and sodium alginate), metabolic substrates and intermediates (α-D-glucose and cellulobiose), storage carbohydrates (amylose and glycogen), and glycoaminoglycans (heparin and chondroitin sulfate A).

Luminescent Conjugated Oligothiophenes

Conjugated oligothiophenes result from the oligomerization of thiophenes, a sulfur heterocycle. Electrons are delocalized along their conjugated backbones, giving these oligomers conductive and/or optical properties. Conjugated oligothiophenes can become conducting when electrons are added or removed from the conjugated π-orbitals via doping. Binding of LCO probe to targets is driven by electrostatic interactions. Also, interaction of these oligomers with target molecules may cause twisting of their backbone structure, resulting in electron distortion and dramatic shifts in their optical properties. As such, the oligothiophenes have a wide range of binding targets which can be individually identified through a corresponding unique oligomer backbone related signal.

The LCOs of the present invention are composed of a core oligothiophene to which side groups can be added to improve the core component's intrinsic function. The core component consists of a pentameric, hexameric, heptameric, octameric, nonameric, decameric or 11-, 12-, 13-, 14- or 15-meric oligothiophene, i.e of polymeric thiophenes consisting of five to fifteen monomers of thiophene. Preferably the component consists of an odd number of monomers as they can hold a larger number of side groups. LCOs of even numbers also target carbohydrates and yield a detection signal but are restricted in the numbers of side groups that may be added.

A wide variety of side groups having different properties can be bound to the core component. For example, the side groups may have anionic, cationic or zwitterionic functionalities. The side groups may be derived from, for example, amino acids, amino acid derivatives, neurotransmitters, monosaccharides, polysaccharides, nucleic acids or combinations and derivatives thereof. The side groups provide the LCOs with molecular properties that increase their affinity for their target compounds and that enable the LCOs to bind to and form complexes with their target compounds. For example, negatively or positively charged side groups enable ionic bonding between the LCO and the target. Ionic and other side group functionalities may also or alternatively enable hydrogen bonding or other forms of non-covalent bonding between the LCO and its target compounds.

Figure 1B:
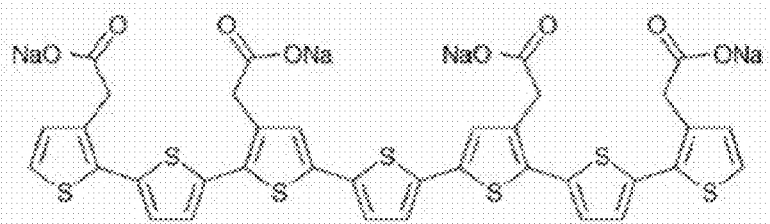
Figure 1B:
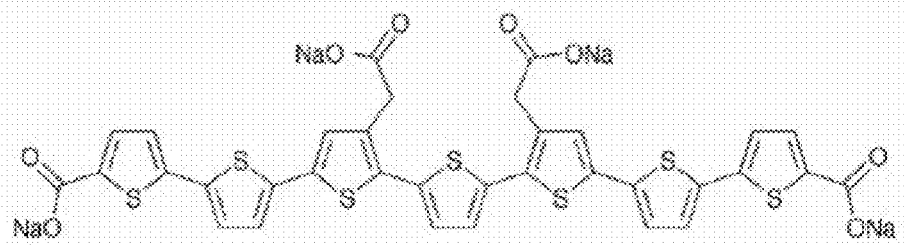

Prototype LCOs for use with the present invention are the pentameric (i.e. having a pentameric oligothiophene core component) and heptameric (i.e. having a heptameric oligothiophene core component) forms shown in FIGS. 1A and 1B, respectively. Examples of pentameric forms include, pHTEA (penta Hydrogen Thiophene Ethanol Amine), pHTIm (penta Hydrogen Thiophene Imidazole), pHTA-Lys (penta Hydrogen Thiophene Acetic acid Lysine), pHTA-Tyr (penta Hydrogen Thiophene Acetic acid Tyrosine) pHTA- Arg (penta Hydrogen Thiophene Acetic acid Arginine), pHTA-Asp (penta Hydrogen Thiophene Acetic acid Aspartic acid), pHTA-His (penta Hydrogen Thiophene Acetic acid Histidine) and pHTA-Glu (penta Hydrogen Thiophene Acetic acid Glutamic acid). Examples of heptameric forms include h-HTAA (hepta Hydrogen Thiophene Acetic Acid) and hFTAA (hepta Formic Thiophene Acetic Acid).

In one aspect the invention comprises a novel compound selected from pHTA-Tyr, pHTA-Arg, pHTA-Asp, pHTA-Glu and pHTA-Lys.

The LCOs of the present disclosure are designed to target carbohydrates while being non-cytotoxic. Each of the prototype LCO probes possess a wide affinity for macromolecules that are related under the category of carbohydrates. They can be related by charge, hydrophobicity, geometry, structure and/or hydrogen donor and acceptor properties. Different probe-carbohydrate pairs possess a unique spectrofluorometric signature, through which the pairs or, if the LCO is known, the carbohydrate can be identified.

Some of the LCOs of the present invention target and yield a detection signal with one specific carbohydrate, but not to other carbohydrates. Such LCOs allow for detection and identification of a single specific carbohydrate. Other LCOs of the present invention target several different carbohydrates and yield a specific detection signal, e.g. a specific excitation/emission spectrum for each target. In the latter case, unique spectral signatures of the LCO for the respective carbohydrate targets allows for identification of the bound component. Such LCOs thus allow for dual or multiple detection and discrimination of several different carbohydrates, using a single LCO. Still other LCOs target multiple carbohydrates and yield an identical or similar detection signal for all target carbohydrates. Such LCOs allow for detection and determination of presence of carbohydrate, but it does not allow for discrimination between or identification of different carbohydrates.

Selected side groups can be added to a core LCO to enhance its sensitivity for a certain target or enhance its ability to discriminate between different targets. Side groups as well as other modifications of the core component can also be used to add other functionalities.

In one embodiment, the LCO is designed such that an electronic signal is directly or indirectly evoked when the probe binds to its target carbohydrate. The electronic signal may originate from an LCO polymer itself, or a coupled conductive organic or inorganic material that translates the geometric change of the LCO into an electrical signal. In said embodiment, probe binding to a carbohydrate is translated to an electronic readout, e.g. by an electrical detector or handheld device. Such detector or device may in addition be arranged to alert a user of the presence of carbohydrate, e.g. as the amount of carbohydrate reaches a defined threshold. As a specific example, such an alert system may for instance be used to alert for presence of biofilm, by detection of the carbohydrate components in biofilm. Much like blood glucose detectors, such detector devices may also be used to indicate the absence, presence or an overwhelming presence of a carbohydrate. Applications include monitoring of blood, foods, patient health or manufacturing pipelines, for good manufacturing practices (GMP) or for quality assurance.

The LCOs as disclosed herein may be provided for use in a variety of media, sensors, devices or products. For example, the LCOs of the present disclosure may be comprised as a liquid additive. The probe can also be printed on surfaces or can be constituted in liquid or aerosol sprays.

Procedures for synthesizing LCOs have been described in Klingstedt, T. et al. (*Org. Biomol, Chem* (2011), 9:8356-8370); Åslund, A et al. (*ACS Chem. Biol*. (2009), 4:673-684; Åslund, A et al. (*Bioconjugate Chem*. (2007), 18:1860-1868) and WO2010/044744. A variety of LCOs that may be used in accordance with the present invention may be prepared by the person skilled in the art, in light of the teachings therein.

Method for Detecting, Identifying and/or Quantifying One or More Carbohydrates

The present invention provides a method for detection, identification and/or quantification of one or more carbohydrates, comprising the steps of:
  contacting an object or a sample with a luminescent conjugated oligothiophene;
  detecting at least one detection signal of the luminescent conjugated oligothiophene; and
  based on said detected detection signal determining the presence, identity and/or quantity of the carbohydrate or carbohydrates on said object or in said sample.

Herein, the expression "detecting, identifying and/or quantifying carbohydrates" includes any type of activity by which the presence, identity and/or quantity of one or more carbohydrates is analyzed. Such activities include, but are not limited to, the identification of unknown carbohydrates within a sample, determination of presence or absence of a carbohydrate or carbohydrates in a sample, quantification of known carbohydrates in a preparation, tracking of carbohydrate conversion from substrate to product during manufacture of a carbohydrate, determination of the location and identity of a carbohydrate in a biological sample or on biological or non-biological surfaces using end time studies or studies in real time. For example, presence of glycoproteins or carbohydrates on cellular surface can be identified and quantified. In the manufacture of new 'green' carbohydrate based materials, the identity and purity of carbohydrates present in such materials can be assessed or verified. The half-life or degradation time of a carbohydrate based material can also be assessed. Similarly, in the manufacture of molecular or biological drugs or pharmaceuticals, the identity and purity of carbohydrates present in such drug or pharmaceutical preparations can be assessed or verified.

The object or sample to be contacted can be any kind of object or sample on or in which it is desirable to evaluate presence, identity or quantity of carbohydrates. A sample may for instance be a chemical or a biological sample, such as a sample from a carbohydrate manufacturing process or a carbohydrate extraction process. A sample may also be a tissue or blood sample in or from a human or animal patient, or a water sample from nature or from an industry, such as a wastewater treatment plant. Monitoring or detecting carbohydrate in/on a tissue sample from a patient includes monitoring or detecting carbohydrate in/on an isolated sample procured from the patient as well as monitoring or detecting a tissue sample in vivo or in situ. An object may for example be an environmental surface, such as the surface of a bench, table, sink, wall, floor, pipe, furniture or any other interior fittings of a hospital, a domestic setting or a factory. It may also be a device such as a medical device, an apparatus, a piece of equipment, a tool, sports gear or other types of gear, or any other device. The binding of the LCO to its target can thus be detected in solution or on a surface, i.e. the method is usable both in solid and liquid assays. A particular advantage of the present invention is that no washing step is required; carbohydrate may be detected directly in unprocessed biological cultures or samples, in vitro, in vivo or in situ. This enables studies of for example carbohydrate behavior and/or formation on objects or in in vitro, in vivo or in situ samples, in real time. Extending the above application to temporal developmental studies, by following a specific signal unique to one carbohydrate, the temporal dynamics of its production can be determined.

The carbohydrate may be analyzed in a pure to relatively pure form, i.e. in a sample comprising mainly the carbohydrate, or may be detected in a more complex form, i.e. where the carbohydrate is present in a more complex mixture such as in a tissue or a biological sample.

The method of the present invention is equally applicable for detection, identification and/or quantification of soluble and insoluble carbohydrates. It is particularly useful for analysis of insoluble carbohydrates, for which no other ease-of-use method is available to date. Carbohydrates that may be analyzed include carbohydrates of any size, i.e. monosaccharides as well as oligosaccharides and larger polysaccharides. The carbohydrate may be isolated from other compounds or may be in a mixture with other compounds or may be intermolecularly or covalently bound to other molecules or structures. Examples of carbohydrates that may be analyzed include, but is not limited to, the carbohydrates demonstrated herein; β-1,3-glucan, cellulose, chitin, sodium-alginate, α-D-glucose, cellulobiose, amylose, glycogen, heparin and chondroitin sulfate A.

The luminescent conjugated oligothiophene (LCO) of the method of the present invention is any LCO as defined herein, comprising homooligomers of thiophene. The conjugated oligothiophene may be a pentameric to 15-meric conjugated oligothiophene, preferably a pentameric or heptameric conjugated oligothiophene. The LCO may also comprise one or more functional side groups such as side groups derived from amino acids, amino acid derivatives, neurotransmitters, monosaccharides, polysaccharides, nucleic acids or other anionic, cationic or zwitterionic side groups. Examples of heptameric conjugated oligothiophene that may be used in the method of the invention include h-FTAA or h-HTAA. Examples of pentameric conjugated oligothiophene that may be used in the method of the invention include pHTA-His, pHTA-Lys, pHTEA, pHTIm, pHTA-Tyr, pHTA-Arg, pHTA-Asp and pHTA-Glu.

Binding of LCO to carbohydrates result in conformational changes of the LCO backbone, which in turn alters intra- and inter-chain processes of the LCO. This conformational change can be detected as a detection signal of the LCO, for example an optical signal such as a fluorometric signal, or an electrical signal such as conductivity. Fluorometric signals can be detected through fluorescence imaging, e.g. using fluorescence confocal microscopy. Alternatively, fluorometric signals may be detected by fluorescence spectroscopy, through excitation and emission spectrums and/or subsequently predefined single excitation and emission sets dependent on the LCO used and/or the carbohydrate to be determined.

This disclosure presents, as proof of concept, spectrofluorometric signals detected by fluorescence spectroscopy. Excitation and emission spectrums and/or subsequently predefined single excitation and emission are used to demonstrate detection sensitivity of LCOs to carbohydrates. Typically, excitation wavelengths lie in the range of 300-500 nm and emission wavelengths lie in the range of 500-700 nm. Analysis of excitation and emission spectrums then feed into the selection of a relevant single excitation and emission set. Each bound carbohydrate induces different twisting of the LCO backbone, resulting in unique spectral signatures for each bound carbohydrate. These unique spectral signatures and signal intensities can be used to distinguish the compounds and thus to determine their identity and quantity in a given sample, liquid or on a surface.

The fluorescence property of a probe has direct effect on the visual color it presents. This may in turn be a parameter for detection. Indirect colorimetric methods in which a detected signal (of any nature) is represented by a pseudo-color, may also serve as means of representing LCO—target binding.

In alternative embodiments the conformational change of the LCO, and thus the binding of the LCO to its target, can be detected by methods which are directed to monitoring deviations in physical parameters. This can non-exclusively include optical (FRET, fluorescence quenching, absorption colormetric, refraction index), material properties (mass, visco-elastic properties, thickness or other properties) and electronic properties (material conductively, ion release or uptake, electron release or uptake, resistance).

In a laboratory setting the binding of the LCO to its carbohydrate target is suitably detected through fluorometric signaling. Methods and devices for fluorometric detection are well known in the art and include fluorescence based microscopy, e.g. fluorescent confocal microscopy and fluorometric plate readers. Such methods and devices are suitable for detection of carbohydrates in solution, culture or tissue samples.

In other settings handheld devices, known in the art, for fluorescence detection may be more suitable, e.g. in an industrial or hospital setting. Such compact devices may also be useful in settings where minimal weight is preferred, such as in the air transport industry or in environmentally friendly vehicles.

In other embodiments the LCO, or a combination of LCOs, is suitably implemented as an active part of a biosensor device and/or chip based sensor, e.g. by immobilizing the LCO(s) on a substrate in a biosensor cell. Modifiable side groups to the core component of the LCO allows for functional adaptation of the LCO probe to use in biosensors as well as for immobilization of the probe to the substrate. A complex between the LCO and the target carbohydrate is formed on the surface of the substrate, the complex formation inducing a physical change that can be transformed into a detection signal. Suitably the biosensor device comprises a receptacle for said substrate as well as detection means. Describing a generic biosensor device, a fluorescence detection biosensor may for example comprise an internal or external light source for generating excitation energy to excite the LCO bound to the target, and an internal or external detector for detecting fluorescence energy generated by the LCO upon excitation.

Based on the detected detection signal several types of information relating to the carbohydrate may be determined.

In one embodiment of the method it is determined whether carbohydrate is present or absent on the object or in the sample. Conclusions of absence or presence of carbohydrate may for instance be drawn by comparing the fluorescent signal from the LCO, as determined e.g. by fluorescence confocal imaging or by fluorescence spectroscopy, gained from the object or sample analyzed, with a negative control sample known to lack carbohydrate. The negative control defines the signal quality of unbound LCO probe. This sets the baseline peak excitation/emission wavelengths and signal magnitude of said unbound probe. The conclusion is drawn that the analyzed sample comprises carbohydrate when a redshift in peak excitation/emission wavelength and/or a simultaneous increase or decrease in signal magnitude is detected. The change in signal properties from the baseline is dependent on the geometric change in probe molecular backbone, arising from the positive binding of the LCO to the carbohydrate. This binding generally leads to a red shift in the peak excitation/emission wavelength and/or an increase in signal magnitude. In some cases the binding of the LCO to the carbohydrate may however lead to quenching of the fluorescent signal from the LCO.

In one embodiment the quantity of carbohydrate that is present on the object or in the sample is determined. For this purpose a calibration curve of the excitation and emission properties of selected LCO across wavelengths with known quantities of a specific carbohydrate is prepared. A single excitation/emission set specific to a carbohydrate is then defined to which a calibration curve is constructed, the calibration curve defining a relationship between excitation/emission detection signal and carbohydrate amount. The magnitude of the detection signal gained from the analyzed object or sample is compared to the calibration curve, and conclusion of the amount of carbohydrate on the analyzed object or in the analyzed sample is drawn.

In another embodiment the identity of carbohydrate or carbohydrates that are present on an object or in a sample is determined. In such an embodiment a LCO capable of distinguishing between different carbohydrates is used to contact the object or sample. The LCO to be used may for instance be selected by being known to bind to one specific carbohydrate, but not to other carbohydrates. A panel of LCOs generated from a library of related LCOs may be applied for the identification of the carbohydrate or carbohydrates present in a sample. Alternatively, the LCO to be used may be able to bind to several types of carbohydrates and yield a specific detection signal, e.g. a specific excitation/emission spectrum for each target. Unique signatures of the LCO for respective carbohydrate targets allows for identification of the bound component. Again in this embodiment, a negative control is used to define the baseline qualities of the signal of unbound probes.

Based on generating a library of spectral signatures of known carbohydrates (positive controls), detecting the absence of characteristic peaks when comparing an unknown sample to this library would suggest the absence of the carbohydrate. Definition of a single excitation/emission set for a particular carbohydrate and subsequent construction of a standard curve would also serve to conclude if said component is absent. A panel of different LCOs that are sensitive to carbohydrates exceedingly different based on structure/charge can also be used to identify a larger pool of polymeric substances.

Alternatively detection of an identified carbohydrate can be enhanced by progressive modification of the LCO prototype. This embodiment would encompass the addition and/or removal of functional chemical groups of the probe to either enhance binding to a specific molecule and/or enhance the fluorescent property of a bound LCO, such that the peak excitation/emission and signal magnitude stands out against other LCO—target pairs.

Uses

Carbohydrates are useful within many areas and are utilized in various applications as for example drugs, supplements, condiments and sweeteners, as well as materials. LCOs are therefore useful as indicators for the production and quality assessment of carbohydrate compounds for such applications. Use of LCOs in carbohydrate detection, identification and quantification will largely be within the pharmaceutical and food industries, as well as in research.

In pharmaceutical industries carbohydrates form a huge library of products. Exemplar groups or products are carbohydrate supplements; biopharmaceutical products; biodegradable materials for medical use; drugs, as well as filters; polymers; and surfaces. Heparin, an important anticoagulant is a well-known carbohydrate for pharmaceutical uses. Similarly, Chondroitin sulfate A, a carbohydrate closely related to heparin, is in market as a health supplement. GMP regulations dictate the importance of showing the identity and purity of a product. The LCO method of the present invention may be applied as a cheap and rapid method to such ends. The LCOs may also be used as indicators showing the synthesis efficiency for the production of important carbohydrates.

In the food and beverage industry, artificial sweeteners are commonly used as sugar substitutes, and to some extent, as cost cutting measures. Carbohydrate based condiments and additives are also increasingly used within the food and beverage industries. Analysis of carbohydrate relevant addition to and alteration of food may become increasingly important as the long term health implications to such molecules are not completely understood. LCOs may therefore be useful in indicating the presence of specific natural carbohydrates, or the presence and identity of substituted molecules that are carbohydrate in nature. Detection of metabolically important carbohydrates such as glucose, amylose and glycogen are shown in this disclosure.

In ready-made and packaged foods, LCOs may be used as indicators which sense a change in food quality when placed in close proximity with said food items. This change may be the detection of the presence of a carbohydrate which gradually appears/becomes detected, as the food deviates from the original quality when initially made.

The LCOs and methods disclosed herein may be used in basic research to study and gain greater understanding of carbohydrate formation, breakdown, and of carbohydrate characteristics. Cellulose conversion into biofuels has been the subject of extensive research. Cellulose is converted to cellulobiose and glucose during the process. This can encompass a wide variety of settings in which the quality and quantity of carbohydrates is relevant. The fluorometric shifts in LCO optical profiles, gained as a carbohydrate substrate is converted to a product, can again provide a cheap and rapid method for the analysis of the efficiency of a synthesis method and the quality of the product formed. LCOs can be applied to track the conversion of any detectable carbohydrate.

LCOs may further be used in biological research for analysis of formation and/or behavior of a carbohydrate containing biological entity such as a cell or a glycoprotein. Using the LCOs of the present invention, such research may be performed in vitro, in vivo or in a live tissue sample in situ.

Probes in this disclosure are sensitive to structural carbohydrates in the extracellular matrix (ECM) of microbial biofilm. Different microbes are known to utilize a variety of possible structural carbohydrates in their ECM, the best known carbohydrates being cellulose, $\beta$-1,3-glucan, chitin and alginate. Carbohydrate based identification of biofilm morphologies and quantity can be a novel and highly accurate approach to biofilm detection. Since the ECM of a biofilm is a heterogeneous organization of insoluble structures, a panel of different LCOs will allow the identification of such insoluble structures. Furthermore, since the composition of biofilm formed from different species of bacteria is believed to be unique, a panel of different LCOs also allows for identification of different bacterial species.

In the plant and foresting industry materials and products (wood, pulp and paper) are primarily carbohydrates (insoluble structural carbohydrates). Wood, pulp, and paper originating from different sources (e.g. different trees) may be detected by profiling the type, quantity and quality of the composed carbohydrates. LCOs with the ability to detect carbohydrates may hold great use to this end. Similarly, the quality of wood, pulp, and paper may be identified using LCOs. This may involve applying LCOs to determine the purity of carbohydrates present.

EXAMPLES

As will be demonstrated below, the ability of the LCOs of the present invention to target not only amyloid proteins but also carbohydrates was surprisingly found while studying biofilm. Biofilms are heterogeneous, complex 3D matrices that comprise a population of microbial cells, which are embedded in an extracellular matrix (ECM). Two well characterized components of the ECM are structural polysaccharides, such as cellulose, and the amyloid protein curli. The following examples demonstrate the ability of LCOs to target and identify the carbohydrate component of biofilms, mammalian storage carbohydrates, metabolic intermediates of carbohydrates and glycosoaminoglycans, both in end point and real time studies, as well as to detect, identify and quantify carbohydrates in complex structures such as biofilm and in more pure form.

Example 1—Detection of Carbohydrate Component in Biofilm

Figure 2:
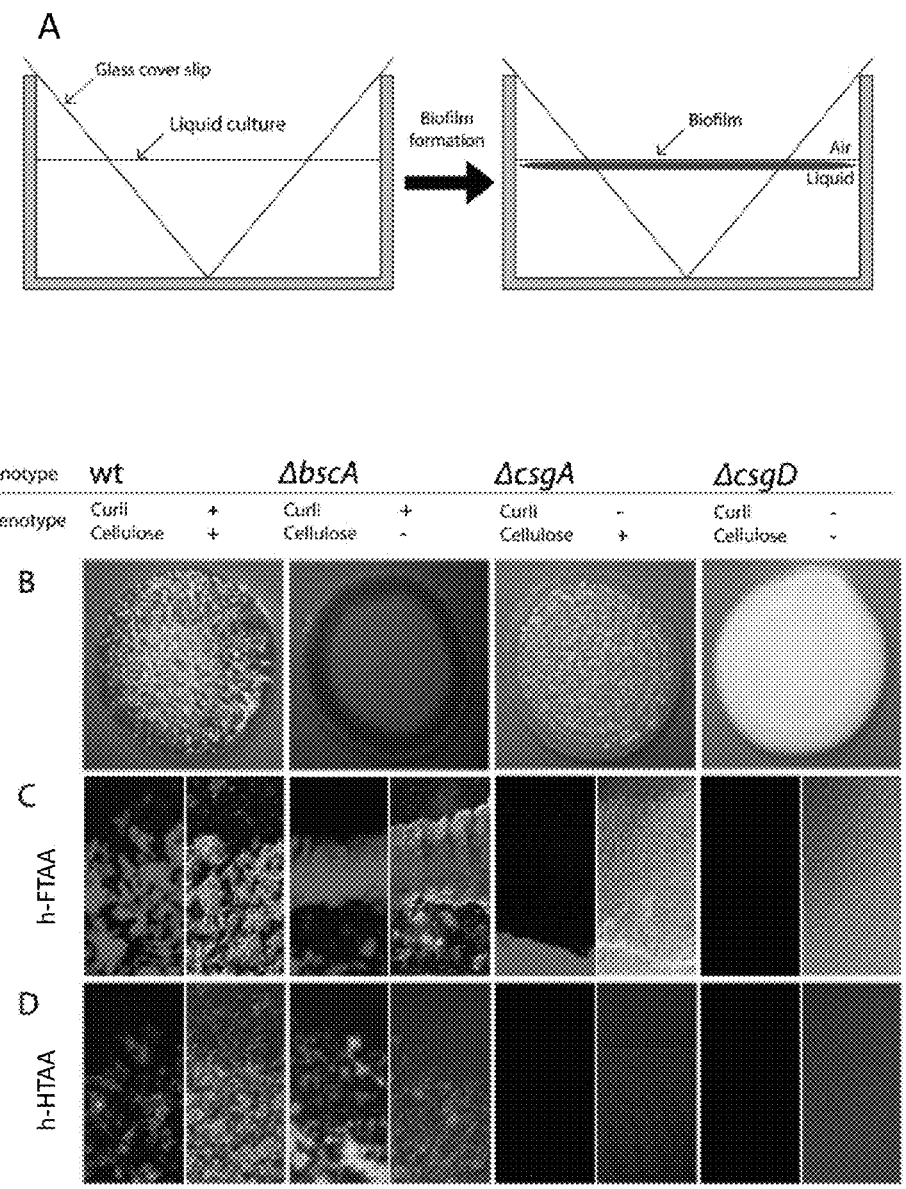
FIG. 2 shows A) a schematic representation of a setup for biofilm formation, occurring at the air-liquid interface, using an inclined glass cover slip set up in the well of a 6 well plate; B) Congo red assay for verification of the biofilm profiles of Salmonella enteritidis (S. enteritidis) 3934 wt and isogenic mutants (ΔbscA, ΔcsgA and ΔcsgD) of known phenotypes; C-D) biofilm morphology of S. enteritidis 3934 wt and isogenic mutants located at the air-liquid interface shown by C) h-FTAA staining and D) h-HTAA staining. Fluorescence confocal analysis (left side) and phase contrast analysis (right side) of the same slide are shown side by side.

Aim of Study:
To demonstrate that the prototype LCO h-FTAA is able to detect a carbohydrate component, i.e. cellulose, in biofilm using confocal analysis.
Study Design:
I. Confirmation of Known Biofilm Morphology Using a Traditional Congo Red Plate Assay
To verify biofilm morphology related to curli and/or cellulose production, *S. enteritidis* wt strain 3934 and isogenic mutants ΔbscA (curli+, cellulose−), ΔcsgA (curli−, cellulose+), and ΔcsgD (curli−, cellulose−) were cultivated on LB agar plates (without salt), supplemented with Congo red (40 μg/ml) and Coomassie brilliant blue G-250 (20 μg/ml). Plates were incubated for 48 h at 28° C.
II. LCO Assay for Fluorescence Analysis of Biofilm and Biofilm Morphology
Glass cover-slips were introduced to the wells of a 6-well plate (according to the set-up shown in FIG. 2A) to provide surfaces for biofilm formation, which at the end of experiment could be easily removed for microscope analysis. To prepare for the biofilm experiment, individual cultures of *S. enteritidis* wt strain 3934 and isogenic mutants ΔbscA, ΔcsgA, and ΔcsgD were grown in LB medium in flasks overnight. Each culture was diluted 100-fold in fresh LB and cultivated in a shaking incubator (230 rpm) at 37° C. to $OD_{600}$=0.6. Cultures were diluted to a culture density of $10^5$ CFU/ml in LB without salt and dispensed into the cover-slip containing 6 well plates in 8 ml aliquots. After incubating the plates for 48 h at 28° C., glass cover-slips were removed and washed twice with PBS before fixation in 4 ml of 4% formaldehyde for 1 h. Fixed samples were washed twice, then immersed in solutions of h-FTAA (2 μg/ml), h-HTAA (2 μg/ml) and PBS respectively, for 30 minutes in the dark. PBS functioned as the negative control, used to assess the level of auto-fluorescence. Treated slides were then washed twice with PBS and mounted with Vectashield® for fluorescence-based confocal laser scanning microscopy analysis. Specifically, the edge of the biofilm formed at the liquid air interface was visualized using the appropriate fluorescence filters. In FIG. 2C-D each slide is represented by an image showing the fluorescence produced by biofilm bound LCOs when excited (left side). The right side is an overlay of an optical inspection of bacterial presence by phase contrast with LCO fluorescence. Phase contrast is a traditional method for visual confirmation of biofilm attachment on surfaces.
Results:
All strains showed the expected morphotype in the Congo red assay (FIG. 2B). The specifics of each strains morphotype are related to their biofilm-forming capacity in terms of curli and cellulose production, and this connection has previously been reported by others.
The LCO assay is able to differentiate curli/cellulose morphologies (FIG. 2C-D, FIG. 2C showing results for h-FTAA and FIG. 2D for h-HTAA). The fluorescent signal from the LCOs (h-FTAA as well as h-HTAA) coincides with visible bacteria aggregates when verified by phase contrast microscopy. With curli present (wt and ΔbscA), the biofilm formed was large and in spaced clusters. When only cellulose is expressed (ΔcsgA), the quantity of cover-slip attached biofilm was greatly reduced, appearing as a thin layer of fluorescent cells. h-FTAA gave a fluorescent signal coinciding with the visible bacteria aggregates produced by cellulose+ and curli− ΔcsgA. ΔcsgD, which lacks both curli and cellulose expression, did not produce detectable biofilm.
Phase contrast microscopy shows superficial characteristics of the biofilm morphology. Optical observations made on the biofilm morphology coincided with that of fluorescence confocal analysis of biofilm bound LCOs.
Conclusion:
The LCO probes bound to and allowed visualisation of biofilms under fluorescence analysis. In addition they allowed for discrimination of the biofilms morphologies originating from the different bacterial phenotypes. The LCO probe h-FTAA was shown to yield a fluorescence detection signal for the strain ΔcsgA, which expresses cellulose but not curli, indicating that h-FTAA is able to detect another component than curli, possibly cellulose.

Example 2—LCOs Generate Unique 'Individualised' Spectral Signatures, Even in Unwashed Cultures, Based on the Curli and Cellulose Content of Biofilm Aim of Study:
To show the ability of LCOs to discriminate between biofilm morphologies comprising different curli and cellulose content, by showing the unique spectral signature LCOs possess with each biofilm.
Study Design:
I. Biofilm Growth in 96 Well Plates
A fresh overnight culture of the clinically derived *S. enteritidis* wt strain 3934 and isogenic mutants (ΔbscA; ΔcsgA and ΔcsgD) was inoculated into fresh LB and cultivated at 37° C. to $OD_{600}$=0.6. After diluting each respective culture with LB (without salt) to a cell density of $10^5$ CFU/ml, it was aliquoted into three separate flasks. h-FTAA (2 μg/ml) and h-HTAA (2 μg/ml) were each added to two of the flasks, whereas PBS, used as a control, was added to the third flask. 50 μl of each culture was next inoculated in triplicates into separate wells of 96-well plates and incubated at 28° C. for 48 hours.
II. Spectral Analysis
After removing the biofilm cultures from the incubator, no processing steps were implemented before the detection of LCO signals. Plates were read using the Synergy Mx Monochromator-Based Multi-Mode Microplate Reader. Excitation spectra of LCOs were collected by exciting the sample from 300 to 500 nm and detecting emission at 545 nm. Emission spectra for curli bound LCOs was collected by reading the emission signal between 500-700 nm when the sample was excited at 405 nm. Emission spectra for cellulose bound LCOs was collected by reading the emission signal between 520-700 nm when the sample was excited at 500 nm.

Figure 3:
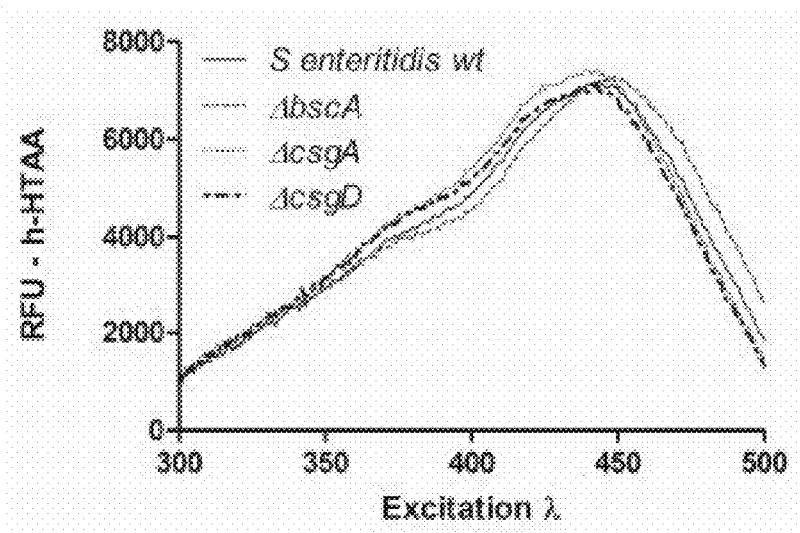
FIG. 3 shows A-B) spectral study of unprocessed biofilm cultures (no washing step performed) of S. enteritidis 3934 wt and isogenic mutants. Excitation spectra of A) h-HTAA and B) h-FTAA in 24 h unprocessed cultures of wt (_), ΔbscA (__), ΔcsgA (...) and ΔcsgD (_.) with emission read at 545 nm; C-D) spectral study of unprocessed (no washing step performed) S. enteritidis 3934 wt and isogenic mutants. Emission spectrum of h-FTAA in 24 h cultures of wt (_), ΔbscA (__), ΔcsgA (...) and ΔcsgD (_.) when excited at C) 405 nm and D) 500 nm.
Figure 3:
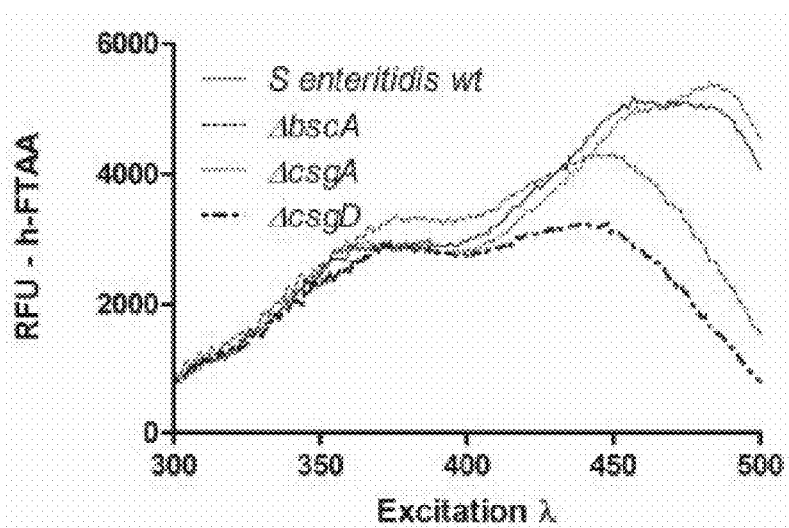
Figure 3:
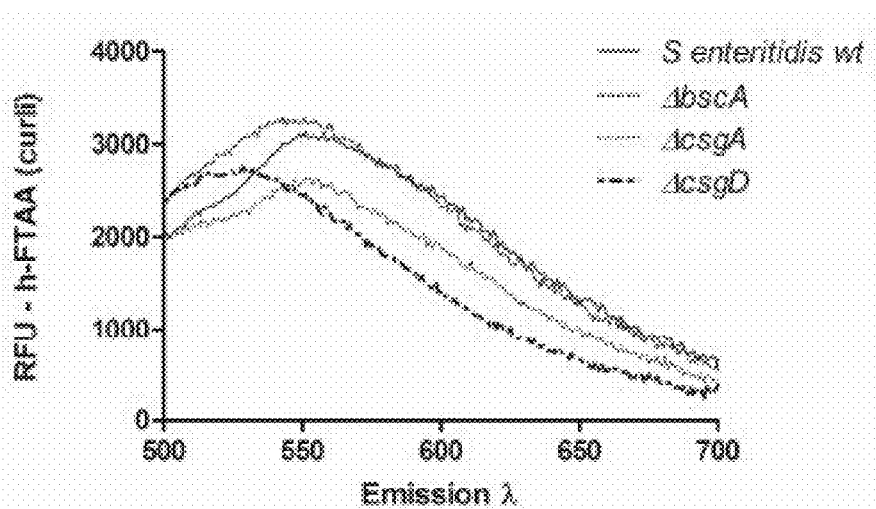
Figure 3:
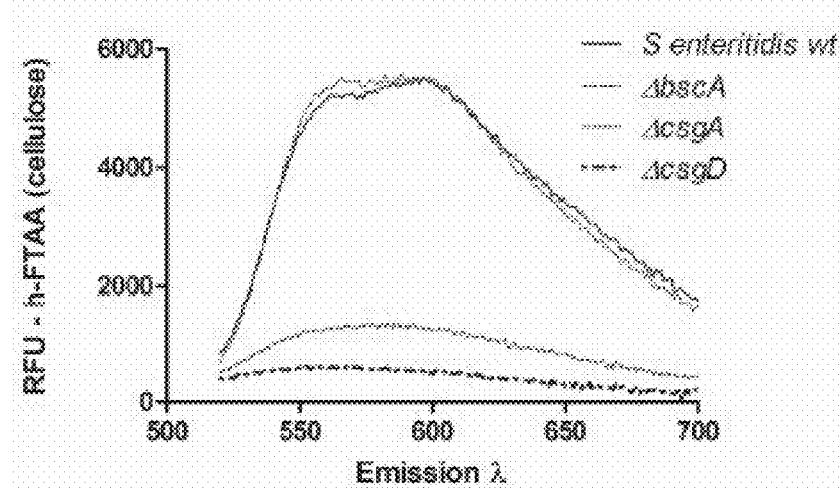

Results:

Spectral profiles of h-HTAA did not differentiate biofilm morphologies formed by the different isogenic mutants (FIG. 3A). Excitation spectra patterns of h-HTAA were identical across all isogenic strains. On the other hand, h-FTAA produced distinguishable spectral patterns of excitation peaks and shoulders with each strain (FIG. 3B). When h-FTAA is excited at 380 nm in the presence of curli (wt and ΔbscA), a unique spike in emission (excitation shoulder) is detected. When h-FTAA is excited at 380 nm in the absence of curli (ΔcsgA ΔcsgD), a spike in emission (excitation shoulder) at ~355 nm is detected instead. Finally, when h-FTAA is excited at 480 nm in the presence of cellulose (wt and ΔcsgA) a unique peak emission is detected.

In overview, h-FTAA in curli positive strains (wt and ΔbscA) had higher emission when excited between 360 nm and 425 nm. The data suggests that excitation of biofilm bound h-FTAA below 425 nm give a signal more specific for h-FTAA bound curli, while excitation above 480 nm gives a signal more specific for h-FTAA bound cellulose.

Using an excitation wavelength of 405 nm for curli and 500 nm for cellulose respectively, the emission spectra for the *S. enteritidis* wt and isogenic strains were analyzed.

When excited at 405 nm (FIG. 3C), h-FTAA in curli positive strains (wt and bscA) had a higher emitted signal intensity at ~556 nm vs curli negative ΔcsgA and ΔcsgD. Comparison of wt, ΔbscA and ΔcsgA against ΔcsgD indicates that when biofilm is expressed there is a red-shift in emission peak from 525 nm to 550-560 nm.

Using an excitation wavelength of 500 nm (FIG. 3D), the emission of h-FTAA was higher across all wavelengths in cellulose positive strains with two prominent peaks in emission at 560 and 600 nm. The unique emission peak at 600 nm formed a cellulose specific signal discriminating its presence from cellulose negative biofilms.

Conclusion:

The LCO h-FTAA produces unique spectral signatures for each biofilm morphology. h-FTAA discriminates biofilm based on unique spectral profiles produced through the interaction with ECM components curli and cellulose. The method does not require physical separation of biofilm from a raw culture. The LCO h-HTAA could not differentiate different biofilm amounts formed by different bacteria phenotypes without washing steps. h-HTAA may be applied better as a general probe for biofilm detection with washing steps akin to Crystal violet. However, h-HTAA has the advantage of being a non-bactericidal probe which can be present in the growth medium throughout the experiment.

Example 3—Verification of Cellulose Specific Spectral Signature

Aim of Study:

To verify the ability of the LCO h-FTAA to target and give a spectral signature for cellulose, and to verify its utility in quantification of cellulose.

Study Design:

Serial two fold dilutions of pure insoluble microcrystalline cellulose suspensions from 6.25 mg/ml to 0.0488 was prepared to which h-FTAA was added to a concentration of 3 μM. 100 μl aliquots was dispensed into a 96 well plate. Plates were read using the Synergy Mx Monochromator-Based Multi-Mode Microplate Reader. Excitation spectra of LCOs were collected by exciting the sample from 300 to 500 nm and detecting emission at 545 nm. Cellulose concentrations shown here are 6.25 mg/ml, 3.125 mg/ml, 1.5625 mg/ml and 0.78125 mg/ml.

Figure 4:
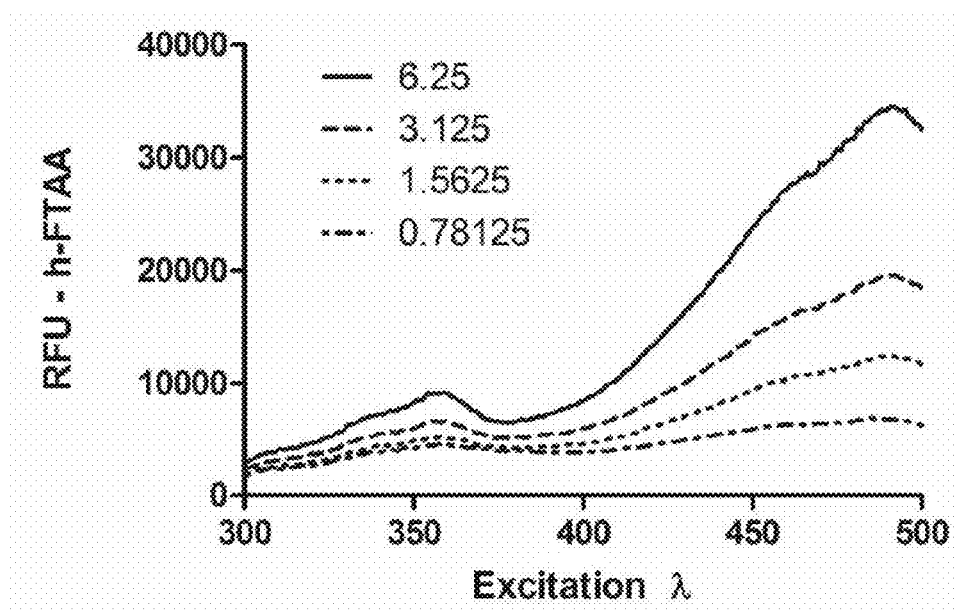
FIG. 4 shows a spectral study of excitation spectrum of pure insoluble microcrystalline cellulose suspensions of 6.25 mg/ml (_) 3.125 mg/ml (__), 1.56 mg/ml (...) and 0.78 mg/ml (_.), when mixed with 3 µg/ml h-FTAA.

Results:

In the presence of pure cellulose, excitation of h-FTAA at ~480 nm gives a peak in emission detected at 545 nm (FIG. 4). This signal intensity increased proportionally with cellulose concentration, verifying that h-FTAA indeed binds cellulose.

Conclusions:

The heptameric LCO h-FTAA can be used for detection and quantification of the carbohydrate cellulose.

Example 4—Real Time Tracking of Biofilm Formation

Aim of Study:

To demonstrate the use of h-FTAA in real-time tracking of biofilm formation, showing the change in biofilm correlated RFU (relative fluorescence unit) over time in relation to culture growth.

Study Design:

The turbidity of a bacterial culture, measured by absorbance at $OD_{600}$, is used to define culture density. Expression of GFP provides a direct representation of bacterial growth and culture density. *S. enteritidis* 3934 wt and isogenic mutants ΔbscA, ΔcsgA, and ΔcsgD were transformed with the plasmid P2777 which carries the gfp gene for a more direct representation of culture density through fluorescence detection. Fresh overnight cultures of each strain was inoculated into fresh LB and cultivated at 37° C. to $OD_{600}$=0.6. After diluting the culture with LB (without salt) to a cell density of $10^5$ CFU/ml, it was aliquoted to two separate flasks. h-FTAA (2 μg/ml) was added to one flask, whereas PBS, used as a control, was added to the second flask. 50 μl of each culture mixture was inoculated in triplicates onto 4 96 well plates and incubated at 28° C. Plates were read for GFP expression as well as curli bound h-FTAA signal (Ex 405 nm, Em 556 nm) and cellulose bound h-FTAA signal (Ex 500 nm, Em 600 nm) in tandem hourly over 48 h, to allow 4 h interval scans of each plate in attempt to avoid bleaching of fluorophores. RFU data of GFP and h-FTAA from the four plates were combined in a single plot to visualize the hourly change in signals over time.

Figure 5:
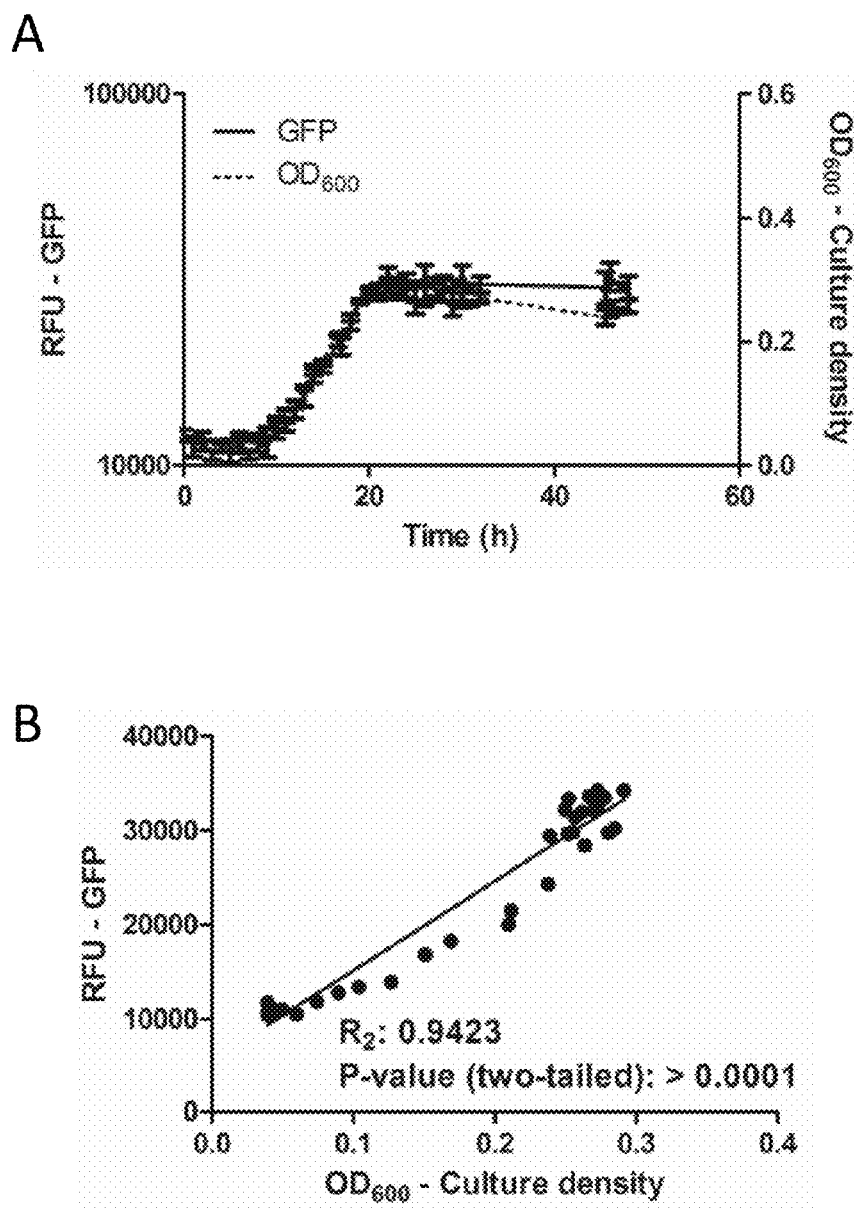
FIG. 5 shows real time tracking of bacterial growth and biofilm formation of S. enteritidis 3934 wt and isogenic mutants ΔbscA, ΔcsgA and ΔcsgD in a 96 well plate. A) comparison of $OD_{600}$ (...) against GFP signal (_) of a wt biofilm culture over 48 hours; B) correlation of $OD_{600}$ against GFP signal; C-F) real-time tracking of biofilm formation of C) S. enteritidis 3934 wt, D) ΔcsgD, E) ΔcsgA and F) ΔbscA, by use of h-FTAA compared to GFP. GFP (_) curli (__) and cellulose (...) signals are shown. Curli is detected with excitation wavelength 405 nm and emission wavelength of 556, and cellulose is detected with excitation wavelength of 500 nm and emission wavelength of 600 nm.
Figure 5:
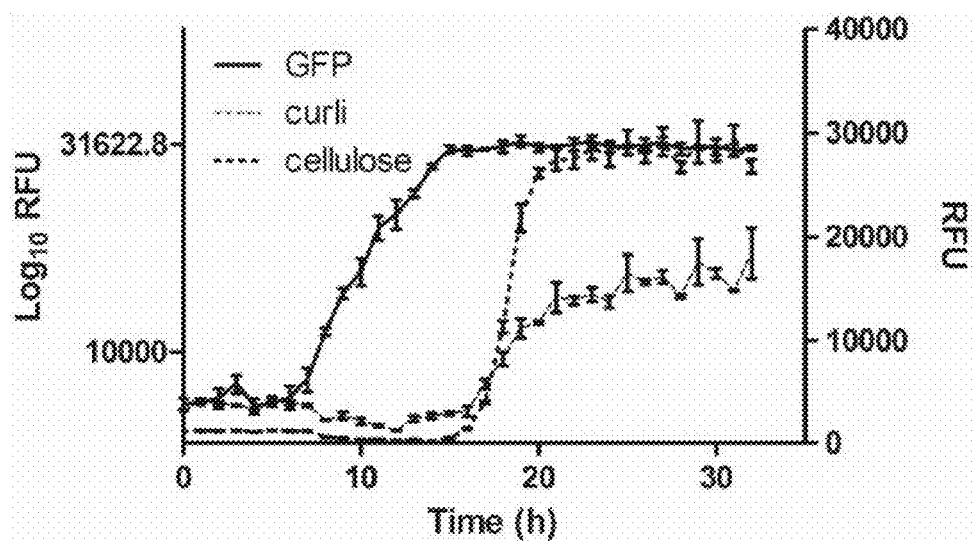
Figure 5:
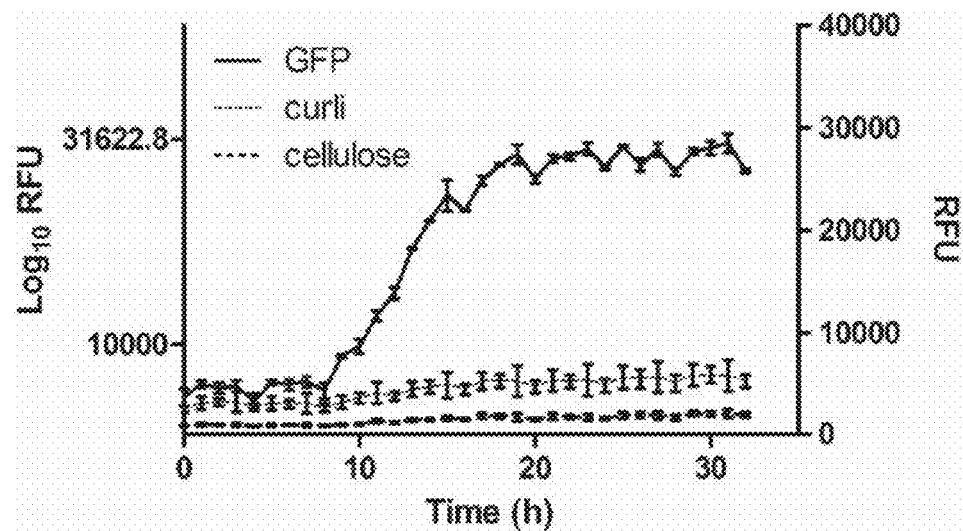
Figure 5:
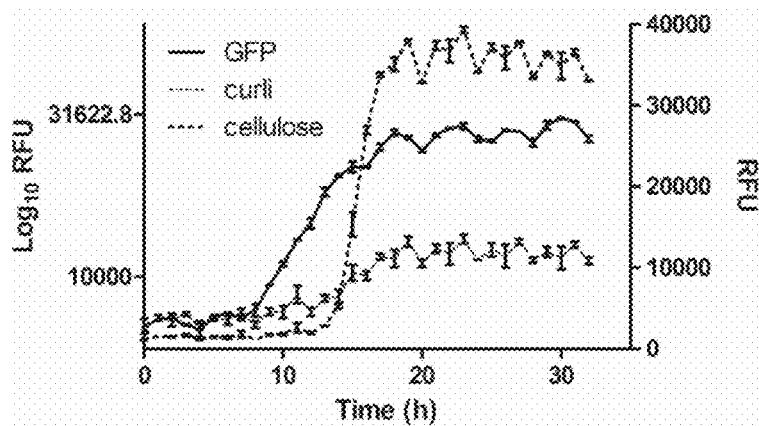
Figure 5:
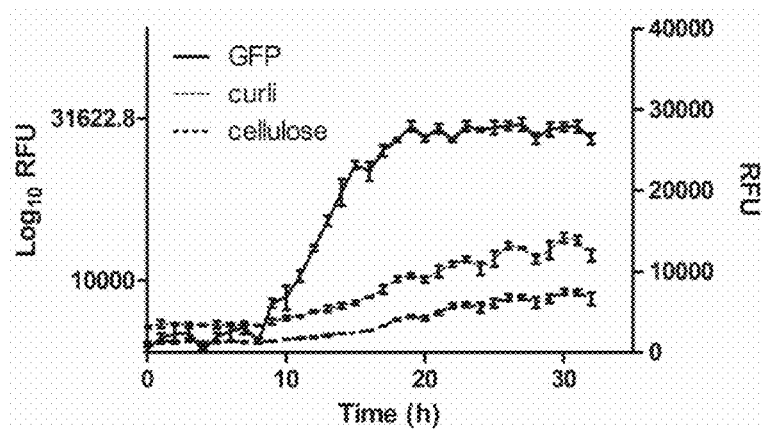

Results:

Comparison of the trend of increase in GFP signal plotted against absorbance at $OD_{600}$ in biofilm cultures showed close correlation (FIG. 5A). Plotting absorbance against GFP signal gave an $R^2$ value of 0.9423 (FIG. 5B), suggesting close correlation of the two signals. This indicated that GFP expression can be used as a means to monitor bacterial growth.

Tracking of h-FTAA signals (FIG. 5C-F) in parallel to GFP fluorescence shows the temporal relationship between biofilm formation and culture growth phases. In *S. enteritidis* wt strain 3934 (FIG. 5C), GFP signal holds constant for the first 6 h (lag phase) before increasing exponentially (logarithmic growth phase) before reaching a plateau at 15 h (stationary phase). In relation, both curli and cellulose signals holds constant for the first 16 h, then increases to a plateau after 22 h. The data implies biofilm formation is initiated towards late exponential phase of culture growth and that cellulose and curli production is simultaneous.

Detected h-FTAA signal does not contain significant bleed through fluorescence from GFP. Observing the fluorescence profile of ΔcsgD hourly over 48 h in a parallel assay, the increase in GFP signal did not cause a increase in curli and cellulose signals (FIG. 5D). The trend observed in excitation and emission sets for curli and cellulose tracking was therefore not the result of signal overflow from the GFP presence.

Analysis of ΔcsgA (FIG. 5E) shows that in the absence of curli expression, biofilm formation kinetics is changed. The onset of peak cellulose expression occurs earlier at 13 h, reaches a plateau at 18 h with higher rate. The RFU intensity at plateau is also higher than the wt when at the same biofilm growth phase. This indicates that cellulose expression may be increased in response to curli absence. Because of the wide emission profile of cellulose bound h-FTAA, a substantial amount of spillover is detected in the curli fluorescence channel.

Figure 6:
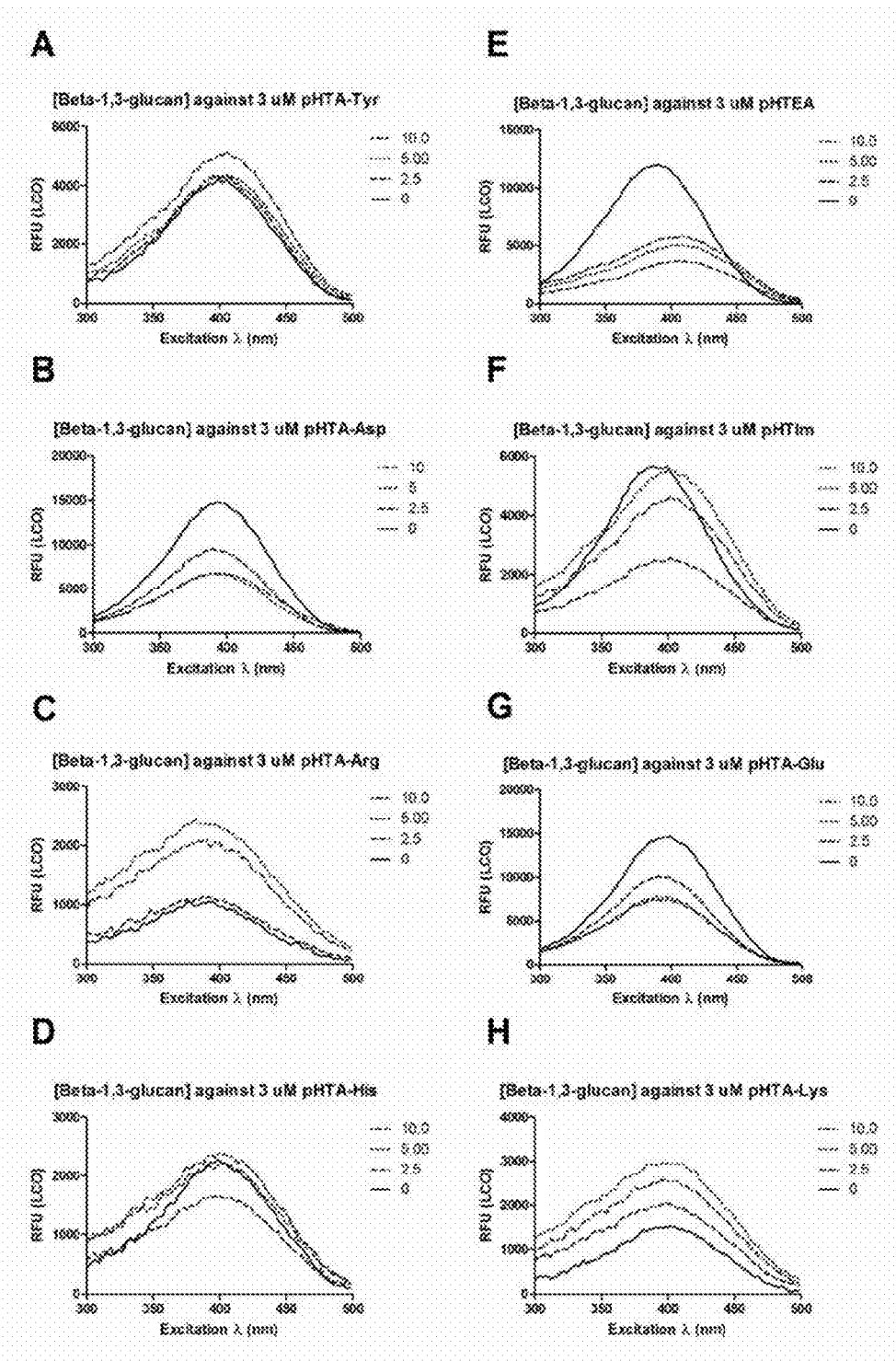
FIG. 6 shows a spectrofluorometric screen of pentameric LCOs against pure insoluble powder carbohydrate suspensions of β-1,3-glucan. 3 µM of each probe was applied to serial two fold dilutions of the insoluble carbohydrate of which the concentration shown here are 10 mg/ml (_.), 5 mg/ml (...) 2.5 mg/ml (__) and 0 mg/ml (_). The excitation spectrum of the probe was analyzed for wavelengths 300-500 nm with emission read at 545 nm. Combinations are as follows; β-1,3-glucan against A) pHTA-Tyr; B) pHTA-Asp; C) pHTA-Arg; D) pHTA-His; E) pHTEA; F) pHTIm; G) pHTA-Glu; and H) pHTA-Lys.
Figure 7:
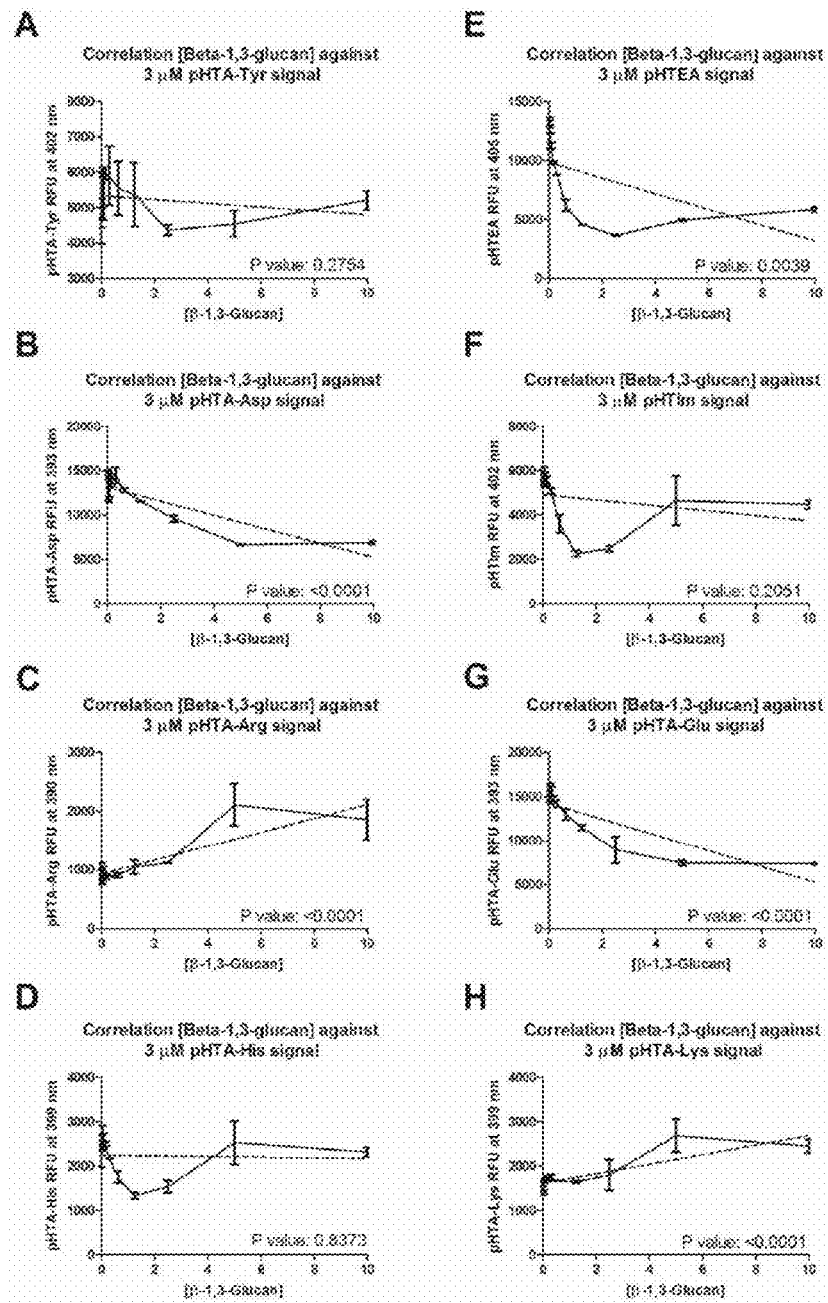
FIG. 7 shows a correlation analysis of the fluorescence intensity of pentameric LCOs against the concentration of pure insoluble powder carbohydrate suspensions of β-1,3-glucan present in the assay. 3 µM of each probe was applied to serial two fold dilutions of the insoluble carbohydrate. Respective probes were excited at wavelengths unique to each probe (specified in figure), and emission was read at 545 nm. Combinations are shown as follows; β-1,3-glucan against A) pHTA-Tyr; B) pHTA-Asp; C) pHTA-Arg; D) pHTA-His; E) pHTEA; F) pHTIm; G) pHTA-Glu; and H) pHTA-Lys. The mean increase in signal (_) with [β-1,3-Glucan] and the fitted regression line (__) is shown.
Figure 8:
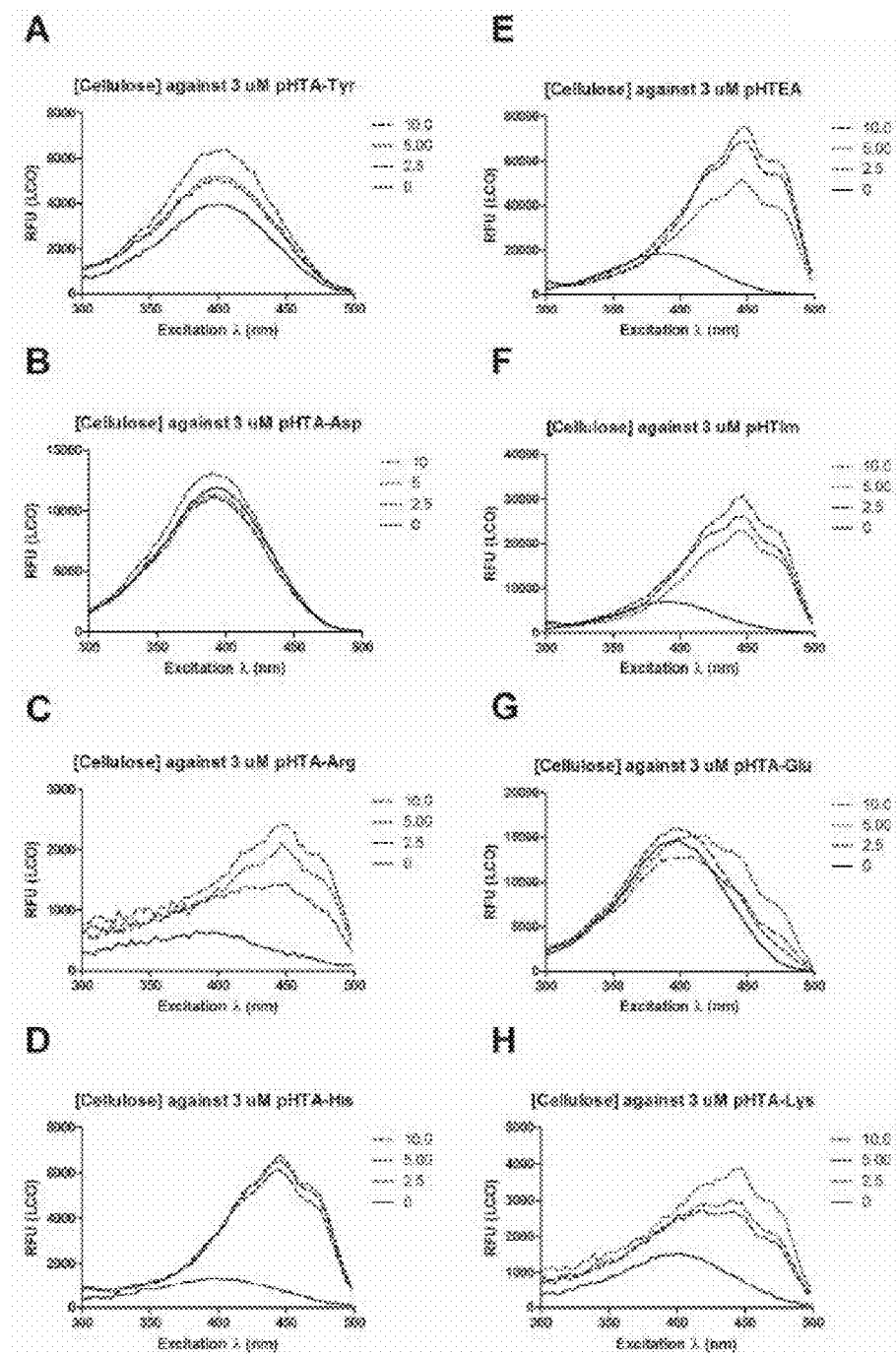
FIG. 8 shows a spectrofluorometric screen of pentameric LCOs against pure insoluble microcrystalline carbohydrate suspensions of cellulose. 3 µM of each probe was applied to serial two fold dilutions of the insoluble carbohydrate of which the concentration shown here are 10 mg/ml (_.), 5 mg/ml (...) 2.5 mg/ml (__) and 0 mg/ml (_). The excitation spectrum of the probe was analyzed for wavelengths 300-500 nm with emission read at 545 nm. Combinations are as follows; cellulose against A) pHTA-Tyr; B) pHTA-Asp; C) pHTA-Arg; D) pHTA-His; E) pHTEA; F) pHTIm; G) pHTA-Glu; and H) pHTA-Lys.
Figure 9:
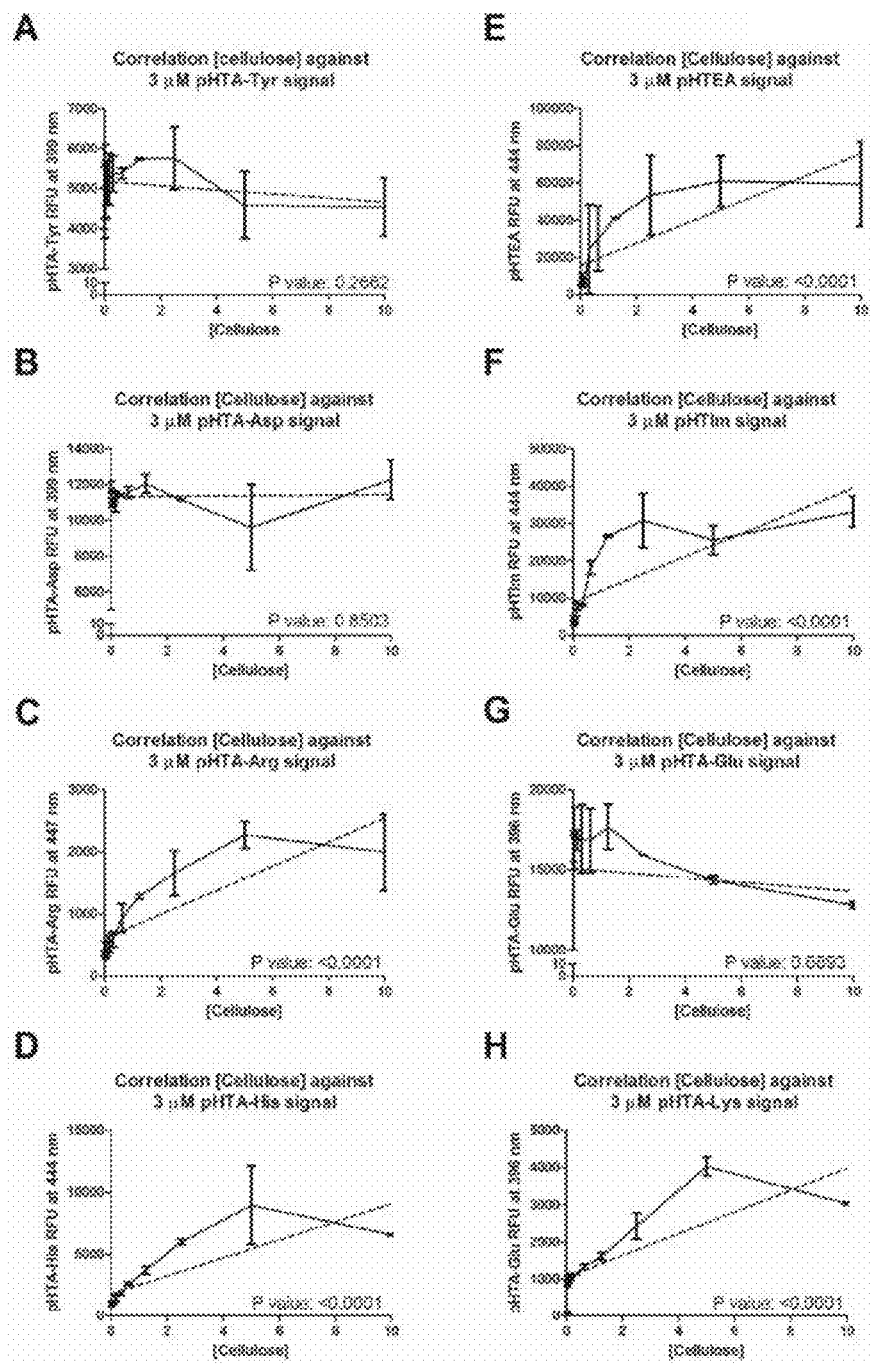
FIG. 9 shows a correlation analysis of the fluorescence intensity of pentameric LCOs against the concentration of pure insoluble microcrystalline carbohydrate suspensions of cellulose present in the assay. 3 µM of each probe was applied to serial two fold dilutions of the insoluble carbohydrate. Respective probes were excited at wavelengths unique to each probe (specified in figure), and emission was read at 545 nm. Combinations are shown as follows; cellulose against A) pHTA-Tyr; B) pHTA-Asp; C) pHTA-Arg; D) pHTA-His; E) pHTEA; F) pHTIm; G) pHTA-Glu; and H) pHTA-Lys. The mean increase in signal (_) with [cellulose] and the fitted regression line (__) is shown.
Figure 10:
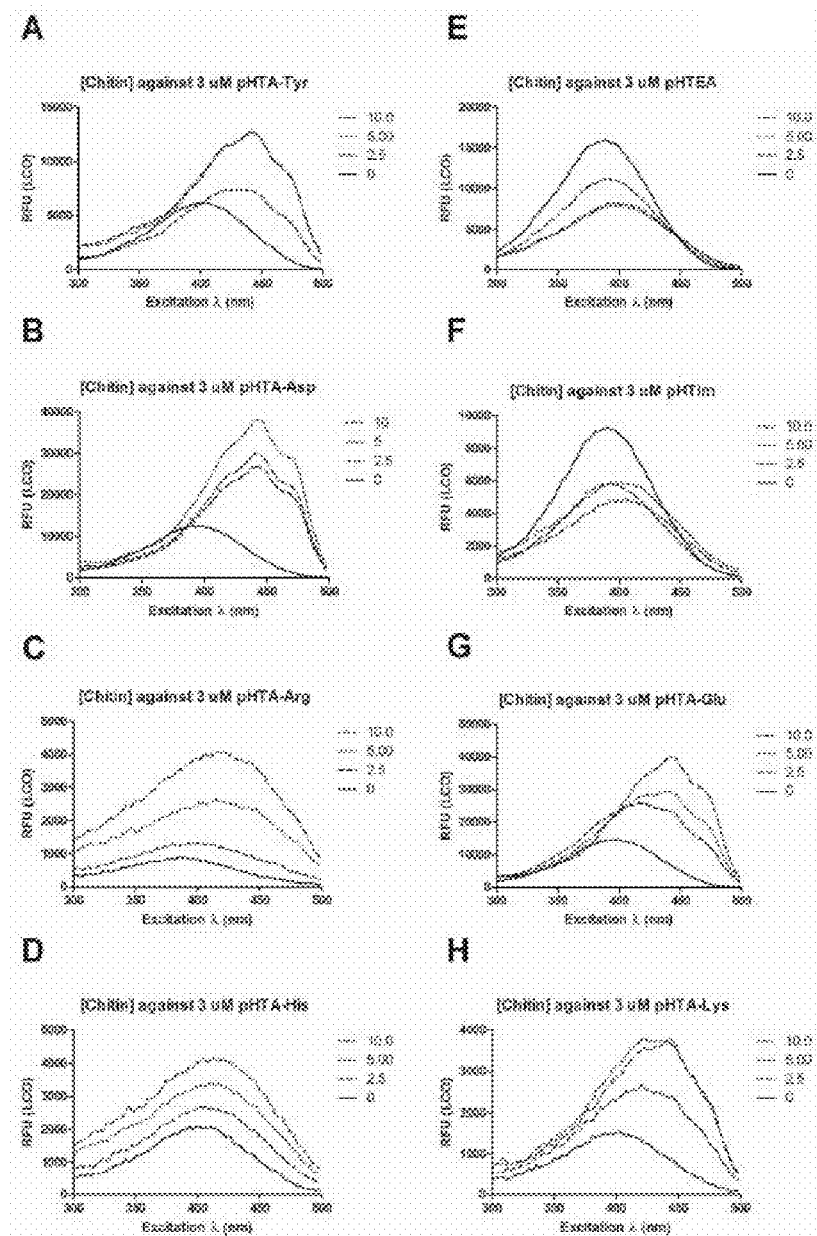
FIG. 10 shows a spectrofluorometric screen of pentameric LCOs against pure insoluble powder carbohydrate suspensions of Chitin. 3 µM of each probe was applied to serial two fold dilutions of the insoluble carbohydrate of which the concentration shown here are 10 mg/ml (_.), 5 mg/ml (...), 2.5 mg/ml (__) and 0 mg/ml (_). The excitation spectrum of the probe was analyzed for wavelengths 300-500 nm with emission read at 545 nm. Combinations are as follows; Chitin against A) pHTA-Tyr; B) pHTA-Asp; C) pHTA-Arg; D) pHTA-His; E) pHTEA; F) pHTIm; G) pHTA-Glu; and H) pHTA-Lys.
Figure 11:
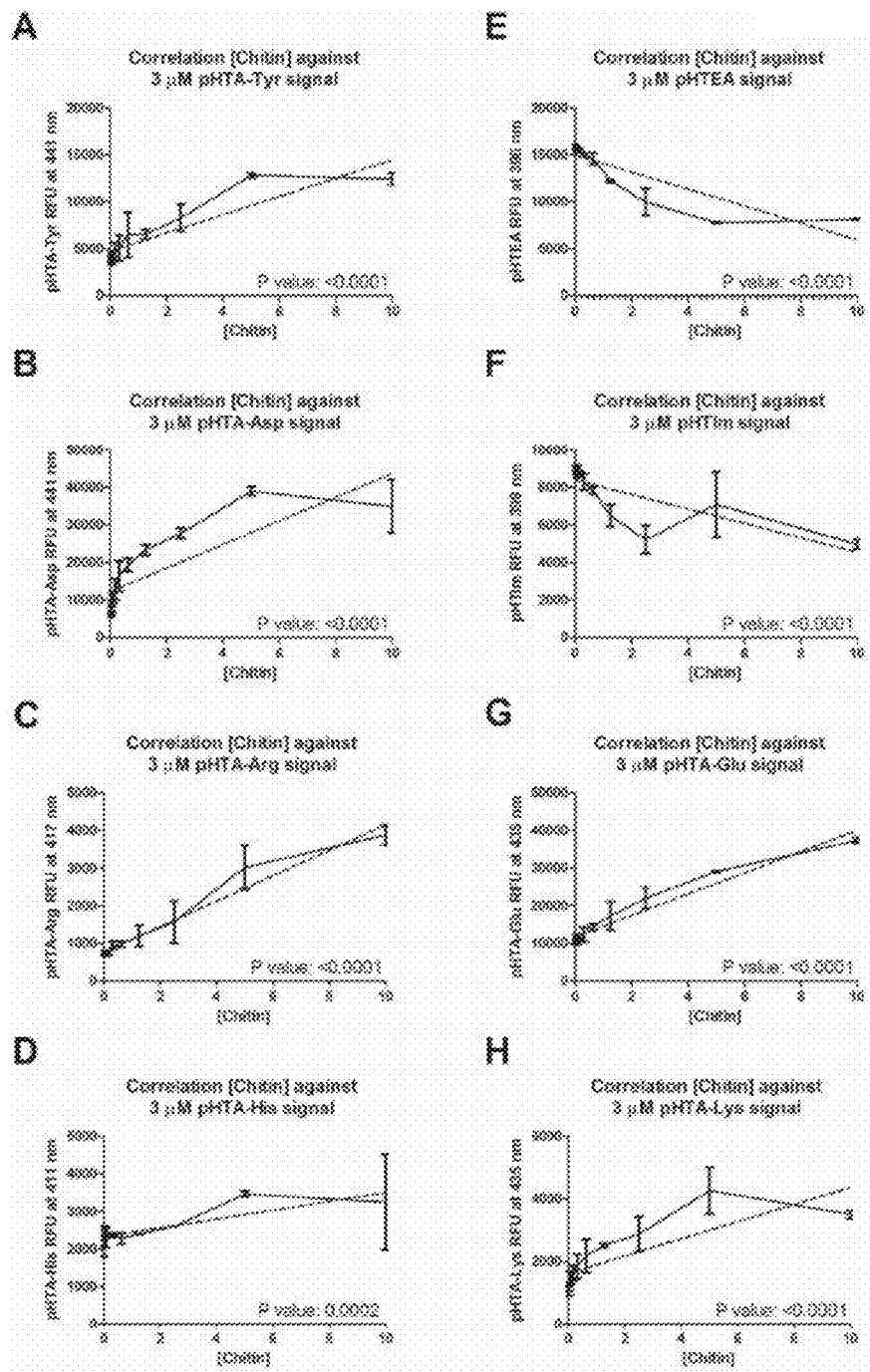
FIG. 11 shows a correlation analysis of the fluorescence intensity of pentameric LCOs against the concentration of pure insoluble powder carbohydrate suspensions of Chitin present in the assay. 3 µM of each probe was applied to serial two fold dilutions of the insoluble carbohydrate. Respective probes were excited at wavelengths unique to each probe (specified in figure), and emission was read at 545 nm. Combinations are shown as follows; Chitin against A) pHTA-Tyr; B) pHTA-Asp; C) pHTA-Arg; D) pHTA-His; E) pHTEA; F) pHTIm; G) pHTA-Glu; and H) pHTA-Lys. The mean increase in signal (_) with [Chitin] and the fitted regression line (__) is shown.
Figure 12:
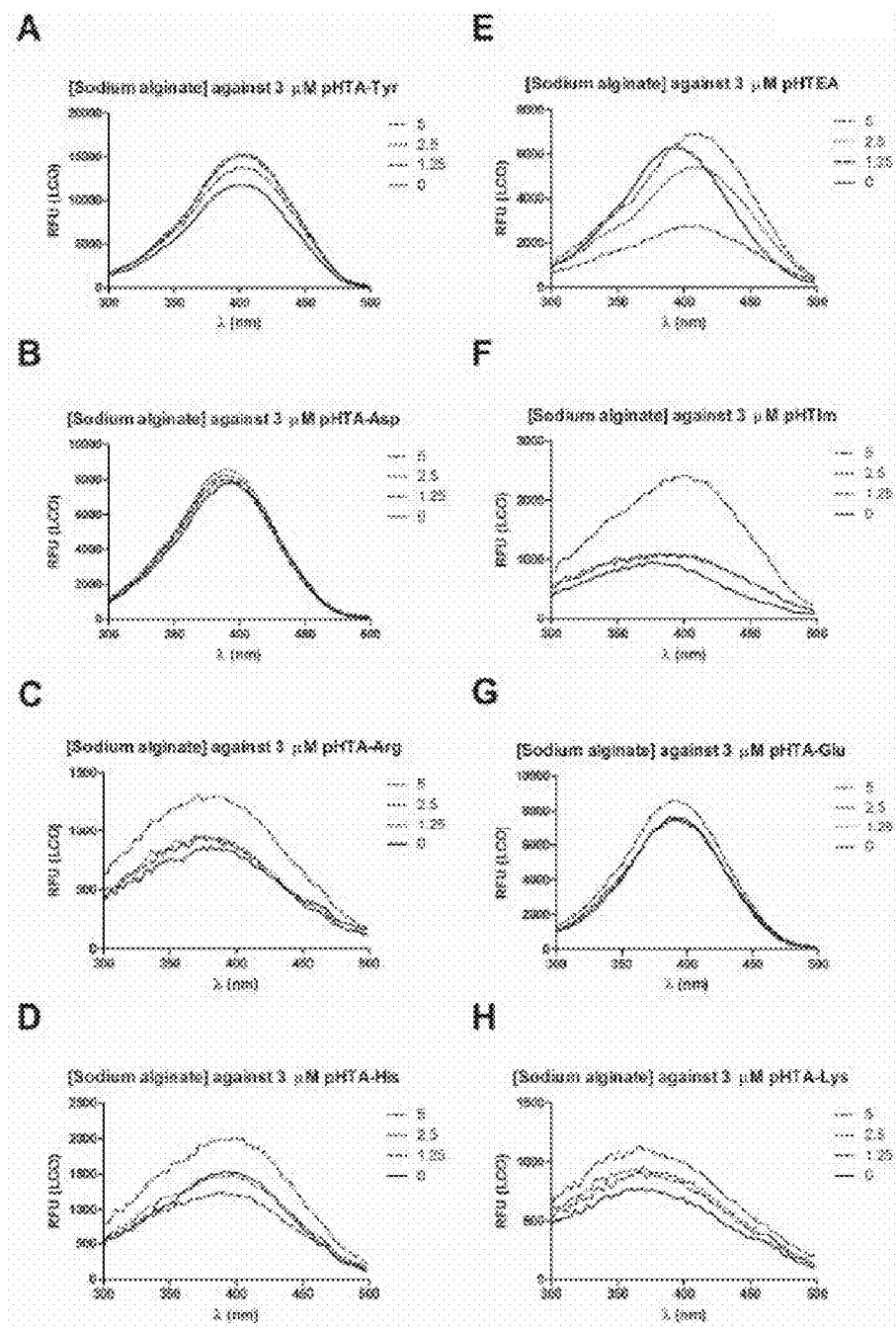
FIG. 12 shows a spectrofluorometric screen of pentameric LCOs against pure insoluble powder carbohydrate suspensions of sodium alginate. 3 µM of each probe was applied to serial two fold dilutions of the insoluble carbohydrate of which the concentration shown here are 5 mg/ml (_.), 2.5 mg/ml (. . . ), 1.25 mg/ml (__) and 0 mg/ml (_). The excitation spectrum of the probe was analyzed for wavelengths 300-500 nm with emission read at 545 nm. Combinations are as follows; sodium alginate against A) pHTA-Tyr; B) pHTA-Asp; C) pHTA-Arg; D) pHTA-His; E) pHTEA; F) pHTIm; G) pHTA-Glu; and H) pHTA-Lys.
Figure 13:
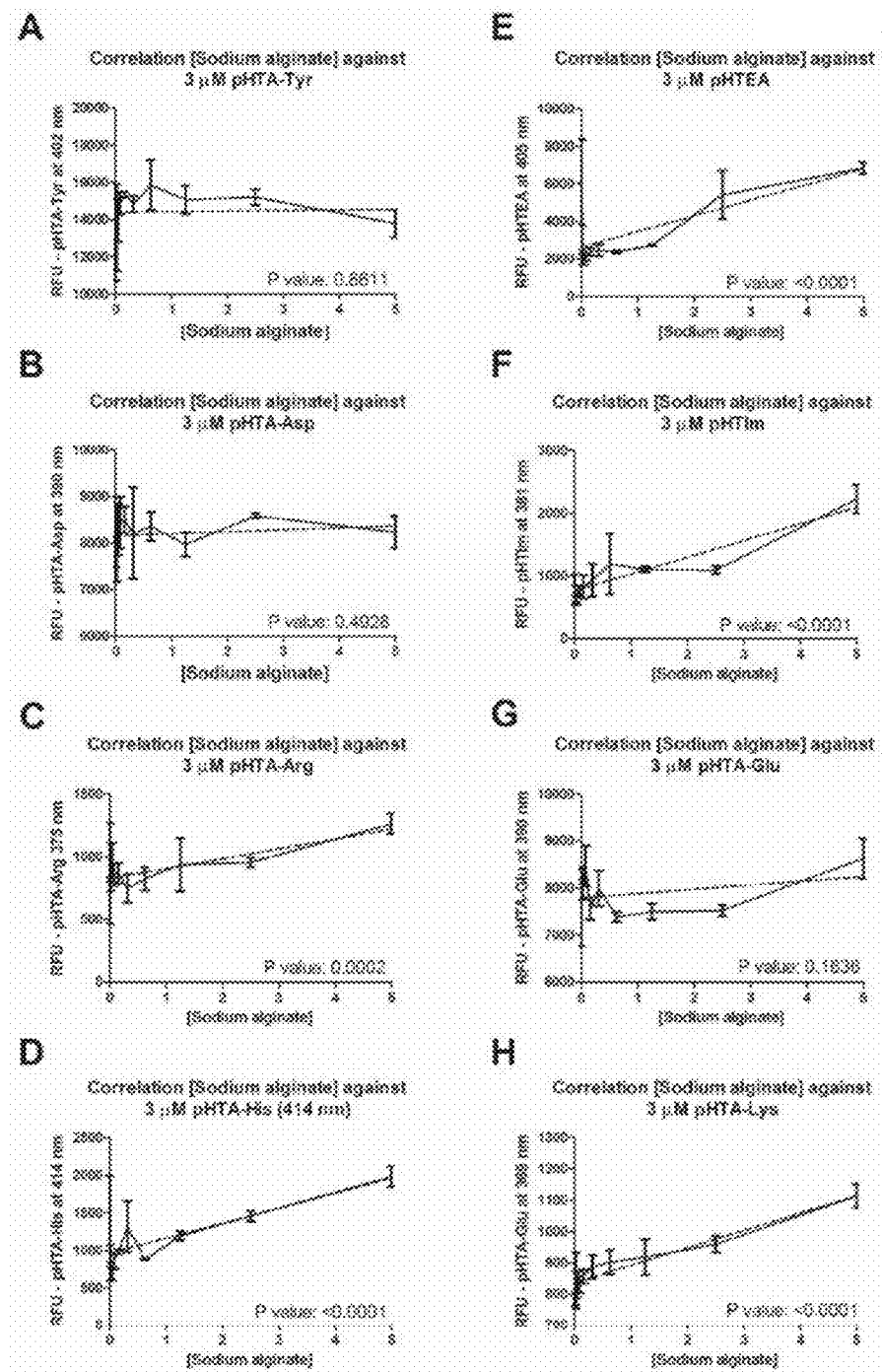
FIG. 13 shows a correlation analysis of the fluorescence intensity of pentameric LCOs against the concentration of pure insoluble powder carbohydrate suspensions of sodium alginate present in the assay. 3 µM of each probe was applied to serial two fold dilutions of the insoluble carbohydrate. Respective probes were excited at wavelengths unique to each probe (specified in figure), and emission was read at 545 nm. Combinations are shown as follows; sodium alginate against A) pHTA-Tyr; B) pHTA-Asp; C) pHTA-Arg; D) pHTA-His; E) pHTEA; F) pHTIm; G) pHTA-Glu; and H) pHTA-Lys. The mean increase in signal (_) with [sodium alginate] and the fitted regression line (__) is shown.
Figure 14:
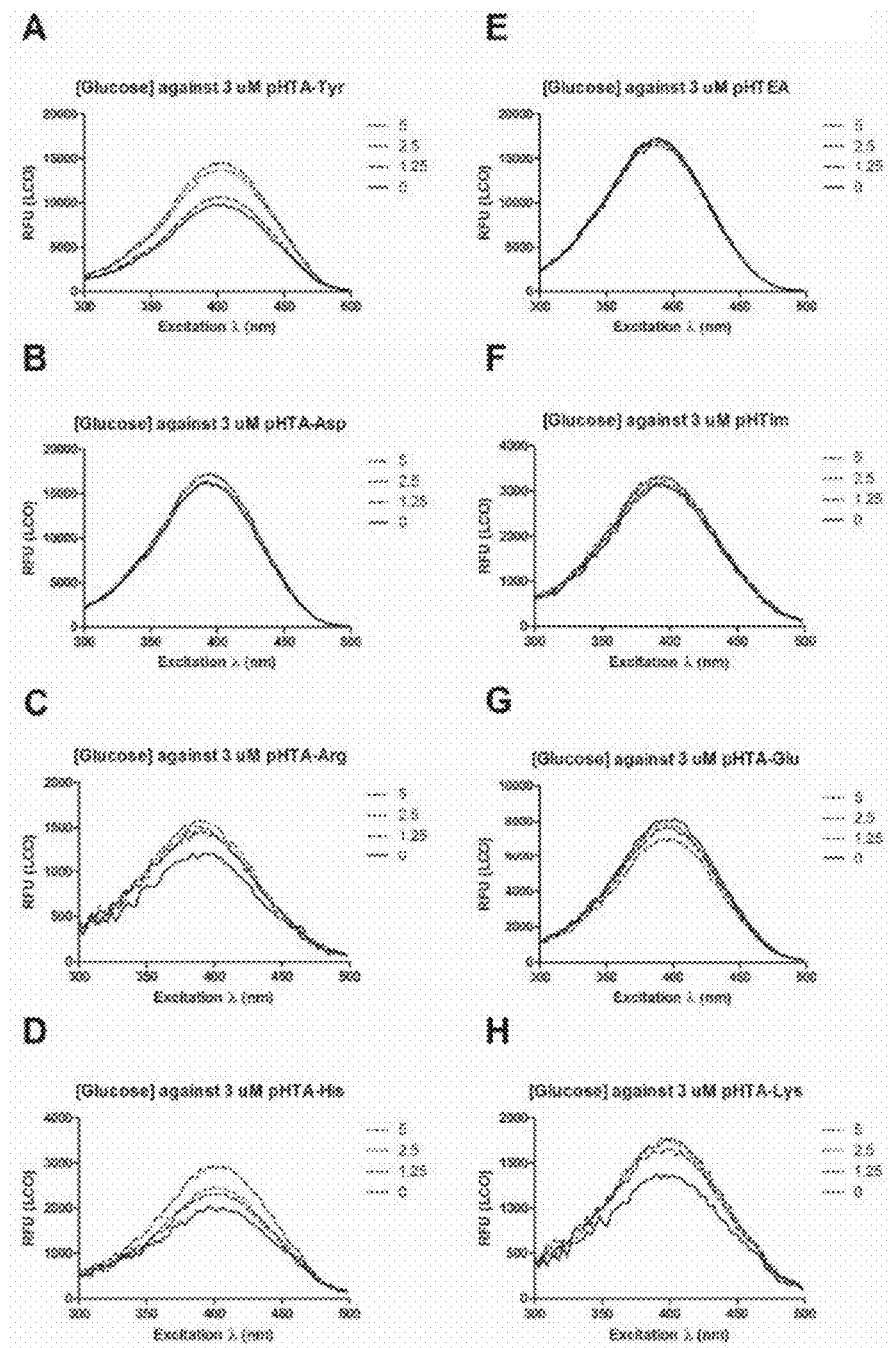
FIG. 14 shows a spectrofluorometric screen of pentameric LCOs against pure carbohydrate solutions of Glucose. 3 µM of each probe was applied to serial two fold dilutions of the carbohydrate of which the concentration shown here are 5 mg/ml (_.), 2.5 mg/ml (. . . ) 1.25 mg/ml (__) and 0 mg/ml (_). The excitation spectrum of the probe was analyzed for wavelengths 300-500 nm with emission read at 545 nm. Combinations are as follows; Glucose against A) pHTA-Tyr; B) pHTA-Asp; C) pHTA-Arg; D) pHTA-His; E) pHTEA; F) pHTIm; G) pHTA-Glu; and H) pHTA-Lys.
Figure 15:
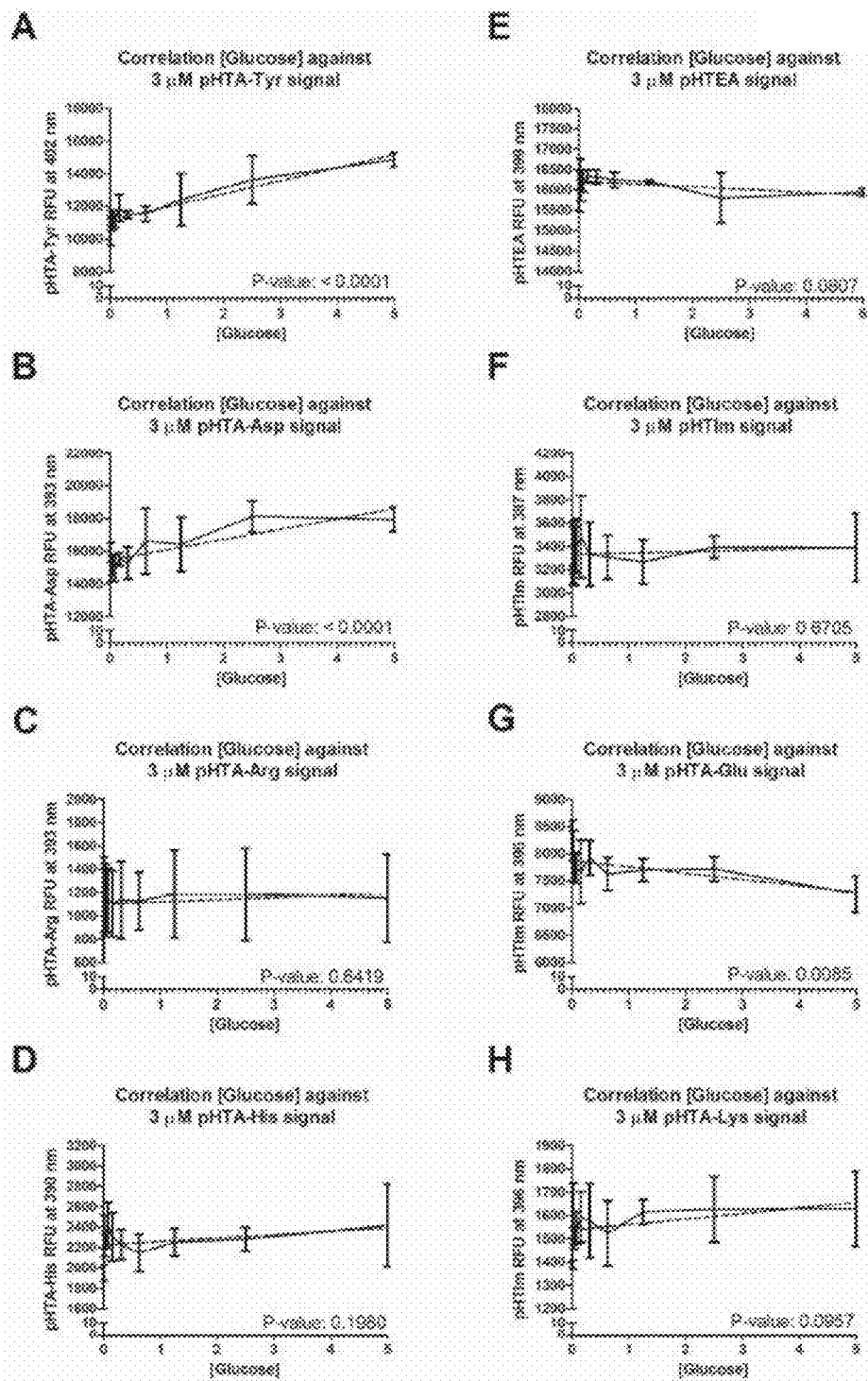
FIG. 15 shows a correlation analysis of the fluorescence intensity of pentameric LCOs against the concentration of pure carbohydrate solutions of Glucose present in the assay. 3 µM of each probe was applied to serial two fold dilutions of the carbohydrate. Respective probes were excited at wavelengths unique to each probe (specified in figure), and emission was read at 545 nm. Combinations are shown as follows; Glucose against A) pHTA-Tyr; B) pHTA-Asp; C) pHTA-Arg; D) pHTA-His; E) pHTEA; F) pHTIm; G) pHTA-Glu; and H) pHTA-Lys. The mean increase in signal (_) with [Glucose] and the fitted regression line (__) is shown.
Figure 16:
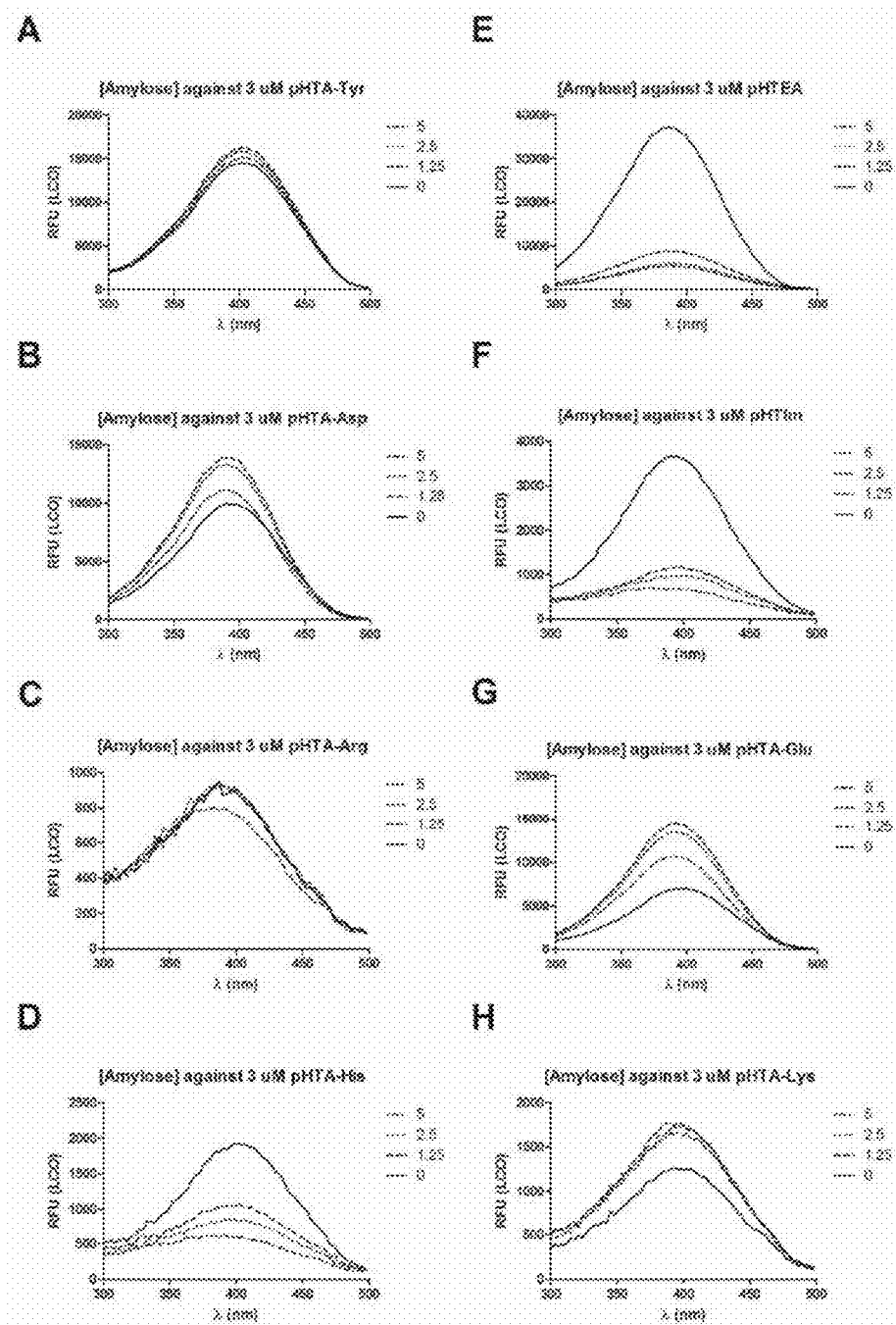
FIG. 16 shows a spectrofluorometric screen of pentameric LCOs against pure carbohydrate suspensions of amylose. 3 µM of each probe was applied to serial two fold dilutions of the carbohydrate of which the concentration shown here are 5 mg/ml (_.), 2.5 mg/ml (. . . ) 1.25 mg/ml (__) and 0 mg/ml (_). The excitation spectrum of the probe was analyzed for wavelengths 300-500 nm with emission read at 545 nm. Combinations are as follows; amylose against A) pHTA-Tyr; B) pHTA-Asp; C) pHTA-Arg; D) pHTA-His; E) pHTEA; F) pHTIm; G) pHTA-Glu; and H) pHTA-Lys.
Figure 17:
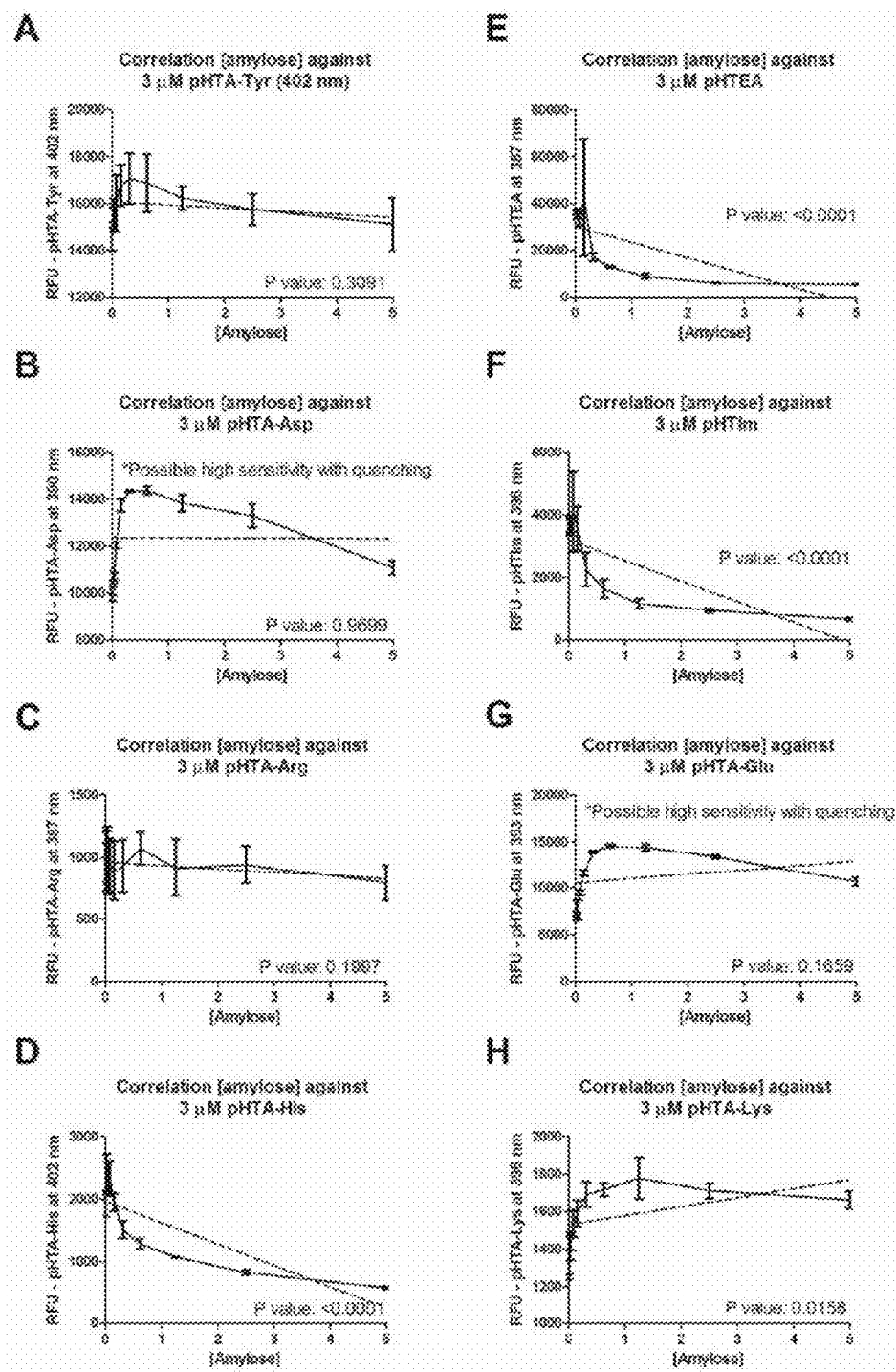
FIG. 17 shows a correlation analysis of the fluorescence intensity of pentameric LCOs against the concentration of pure carbohydrate suspensions of amylose present in the assay. 3 µM of each probe was applied to serial two fold dilutions of the carbohydrate. Respective probes were excited at wavelengths unique to each probe (specified in figure), and emission was read at 545 nm. Combinations are shown as follows; amylose against A) pHTA-Tyr; B) pHTA-Asp; C) pHTA-Arg; D) pHTA-His; E) pHTEA; F) pHTIm; G) pHTA-Glu; and H) pHTA-Lys. The mean increase in signal (_) with [Amylose] and the fitted regression line (__) is shown.
Figure 18:
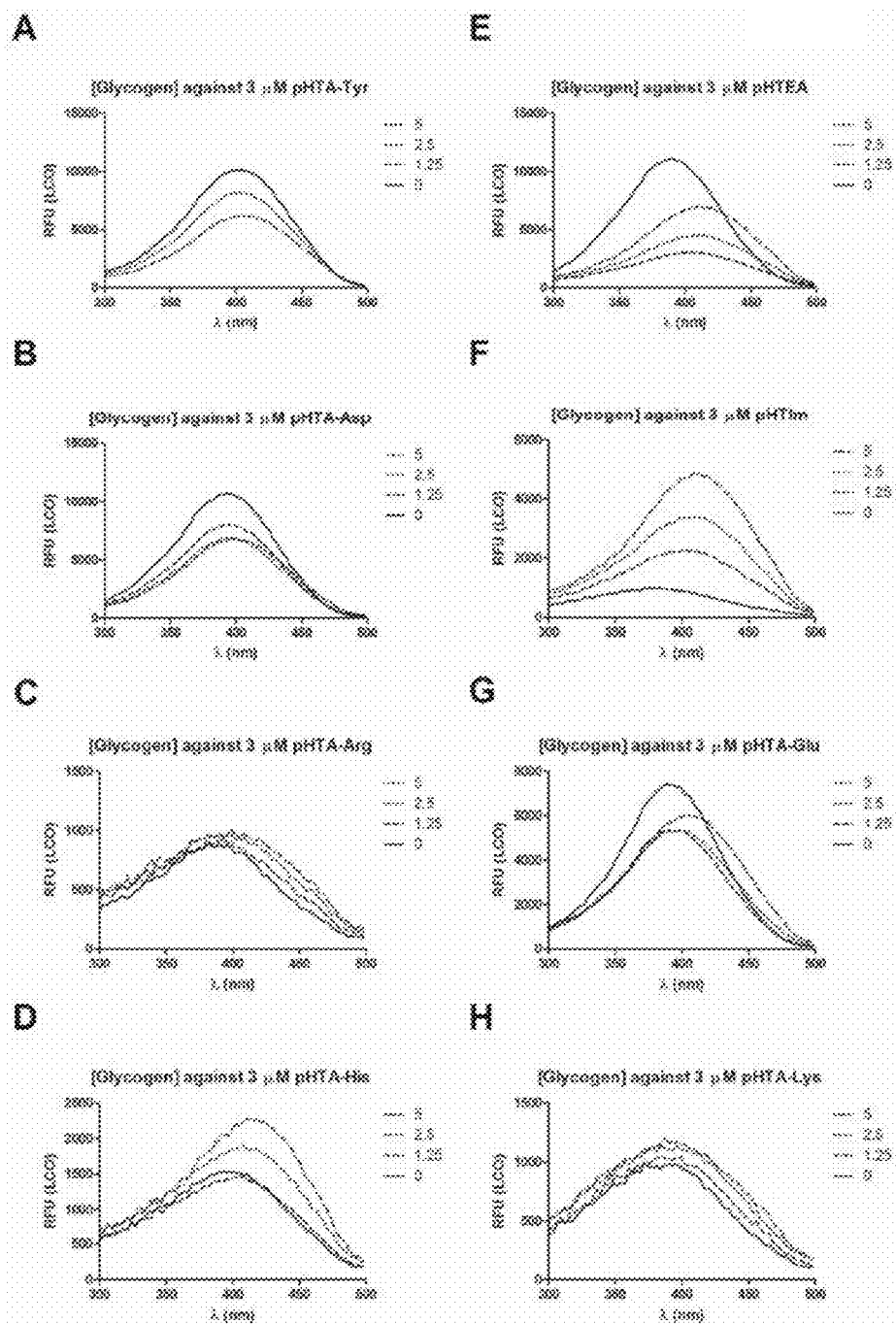
FIG. 18 shows a spectrofluorometric screen of pentameric LCOs against pure carbohydrate suspensions of glycogen. 3 µM of each probe was applied to serial two fold dilutions of the carbohydrate of which the concentration shown here are 5 mg/ml (_.), 2.5 mg/ml (. . . ), 1.25 mg/ml (__) and 0 mg/ml (_). The excitation spectrum of the probe was analyzed for wavelengths 300-500 nm with emission read at 545 nm. Combinations are as follows; glycogen against A) pHTA-Tyr; B) pHTA-Asp; C) pHTA-Arg; D) pHTA-His; E) pHTEA; F) pHTIm; G) pHTA-Glu; and H) pHTA-Lys.
Figure 19:
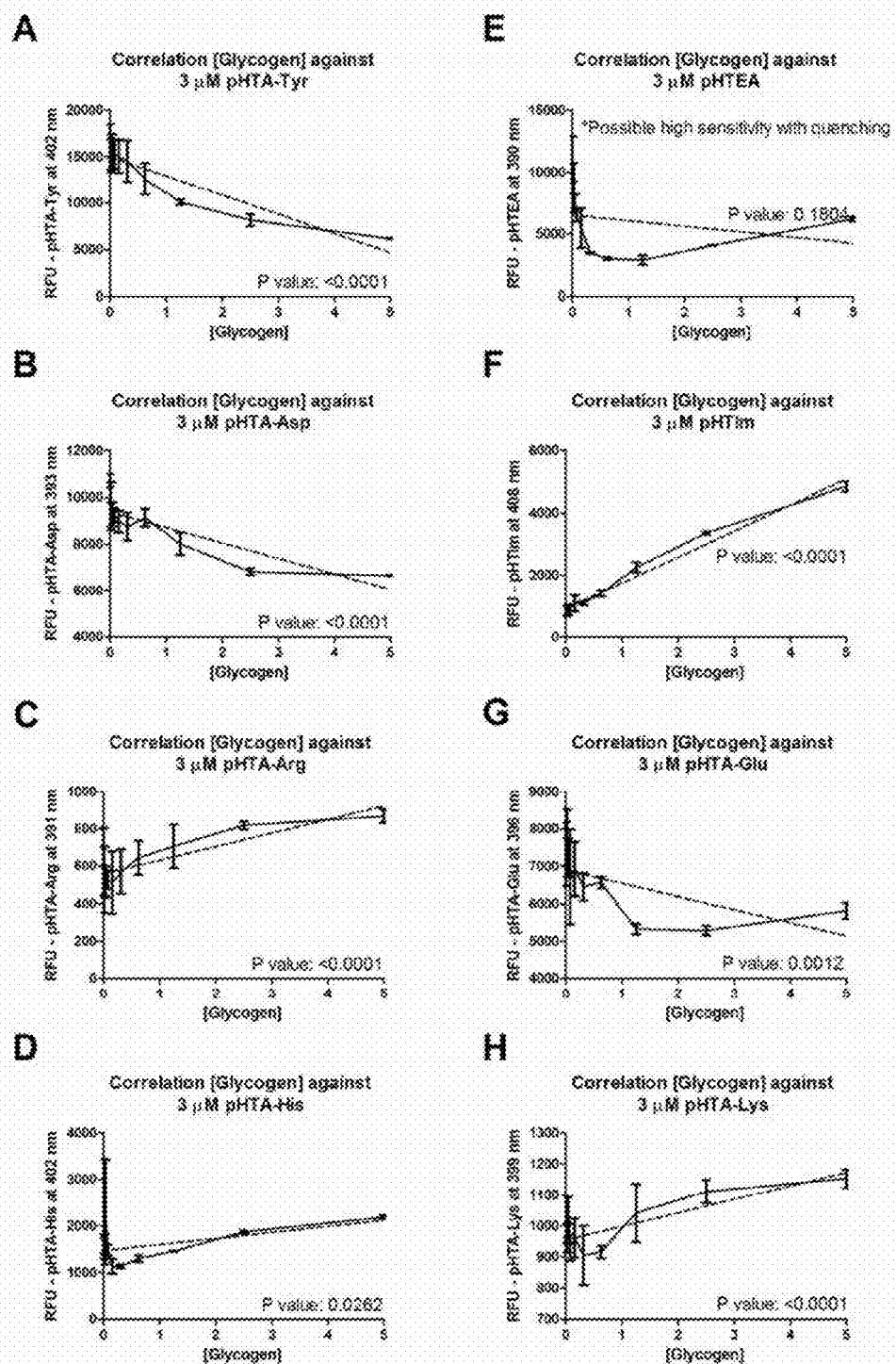
FIG. 19 shows a correlation analysis of the fluorescence intensity of pentameric LCOs against the concentration of pure carbohydrate suspensions of glycogen present in the assay. 3 µM of each probe was applied to serial two fold dilutions of the carbohydrate. Respective probes were excited at wavelengths unique to each probe (specified in figure), and emission was read at 545 nm. Combinations are shown as follows; glycogen against A) pHTA-Tyr; B) pHTA-Asp; C) pHTA-Arg; D) pHTA-His; E) pHTEA; F) pHTIm; G) pHTA-Glu; and H) pHTA-Lys. The mean increase in signal (_) with [glycogen] and the fitted regression line (__) is shown.
Figure 20:
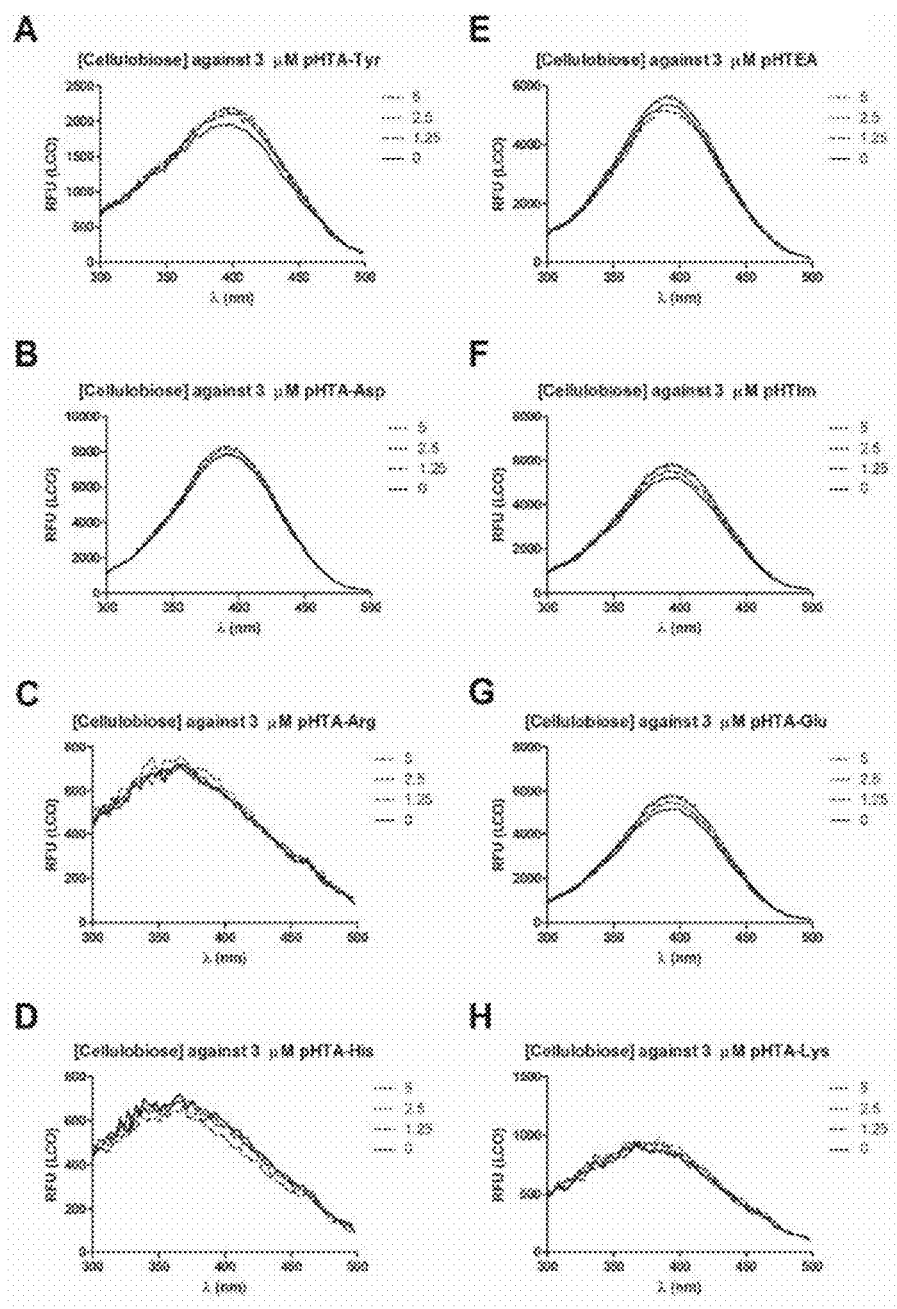
FIG. 20 shows a spectrofluorometric screen of pentameric LCOs against pure carbohydrate solutions of cellulobiose. 3 µM of each probe was applied to serial two fold dilutions of the carbohydrate of which the concentration shown here are 5 mg/ml (_.), 2.5 mg/ml (. . . ) 1.25 mg/ml (__) and 0 mg/ml (_). The excitation spectrum of the probe was analyzed for wavelengths 300-500 nm with emission read at 545 nm. Combinations are as follows; cellulobiose against A) pHTA-Tyr; B) pHTA-Asp; C) pHTA-Arg; D) pHTA-His; E) pHTEA; F) pHTIm; G) pHTA-Glu; and H) pHTA-Lys.
Figure 21:
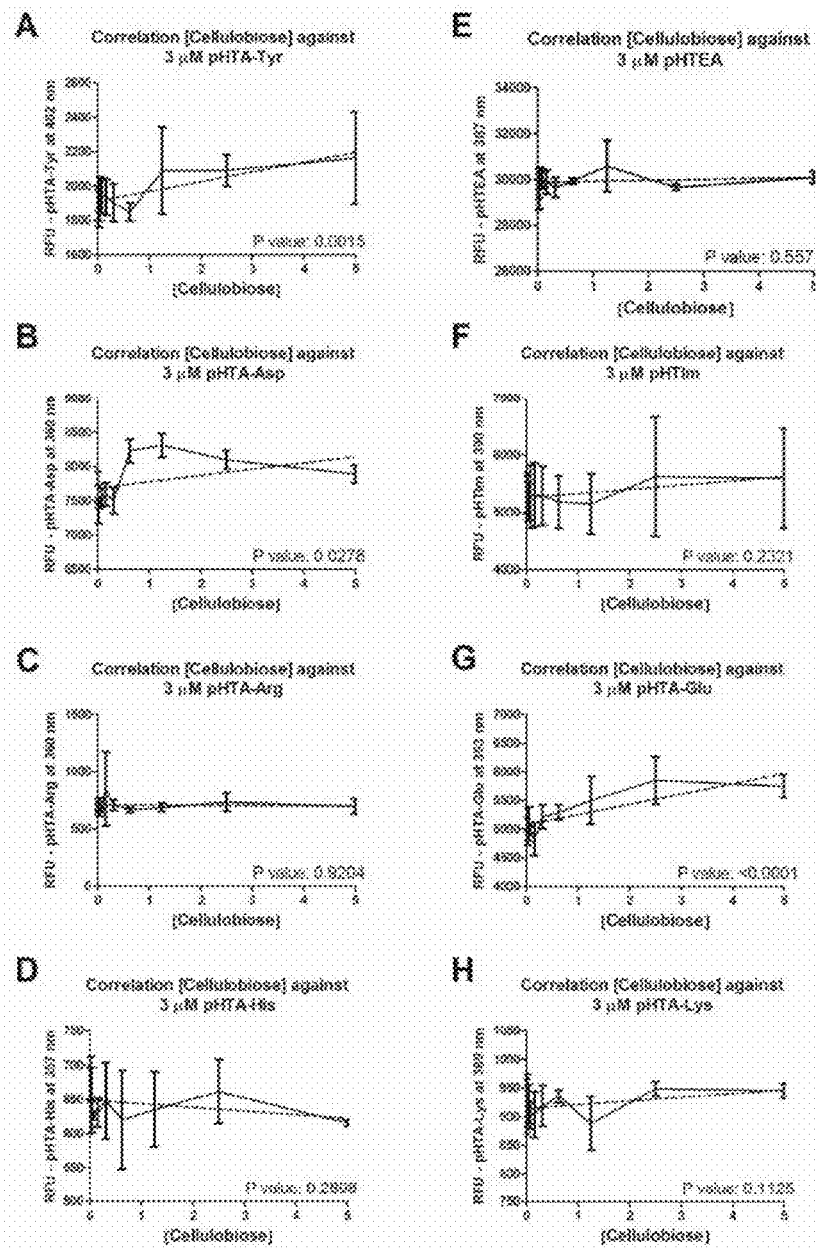
FIG. 21 shows a correlation analysis of the fluorescence intensity of pentameric LCOs against the concentration of pure carbohydrate solutions of cellulobiose present in the assay. 3 µM of each probe was applied to serial two fold dilutions of the carbohydrate. Respective probes were excited at wavelengths unique to each probe (specified in figure), and emission was read at 545 nm. Combinations are shown as follows; cellulobiose against A) pHTA-Tyr; B) pHTA-Asp; C) pHTA-Arg; D) pHTA-His; E) pHTEA; F) pHTIm; G) pHTA-Glu; and H) pHTA-Lys. The mean increase in signal (_) with [cellulobiose] and the fitted regression line (__) is shown.
Figure 22:
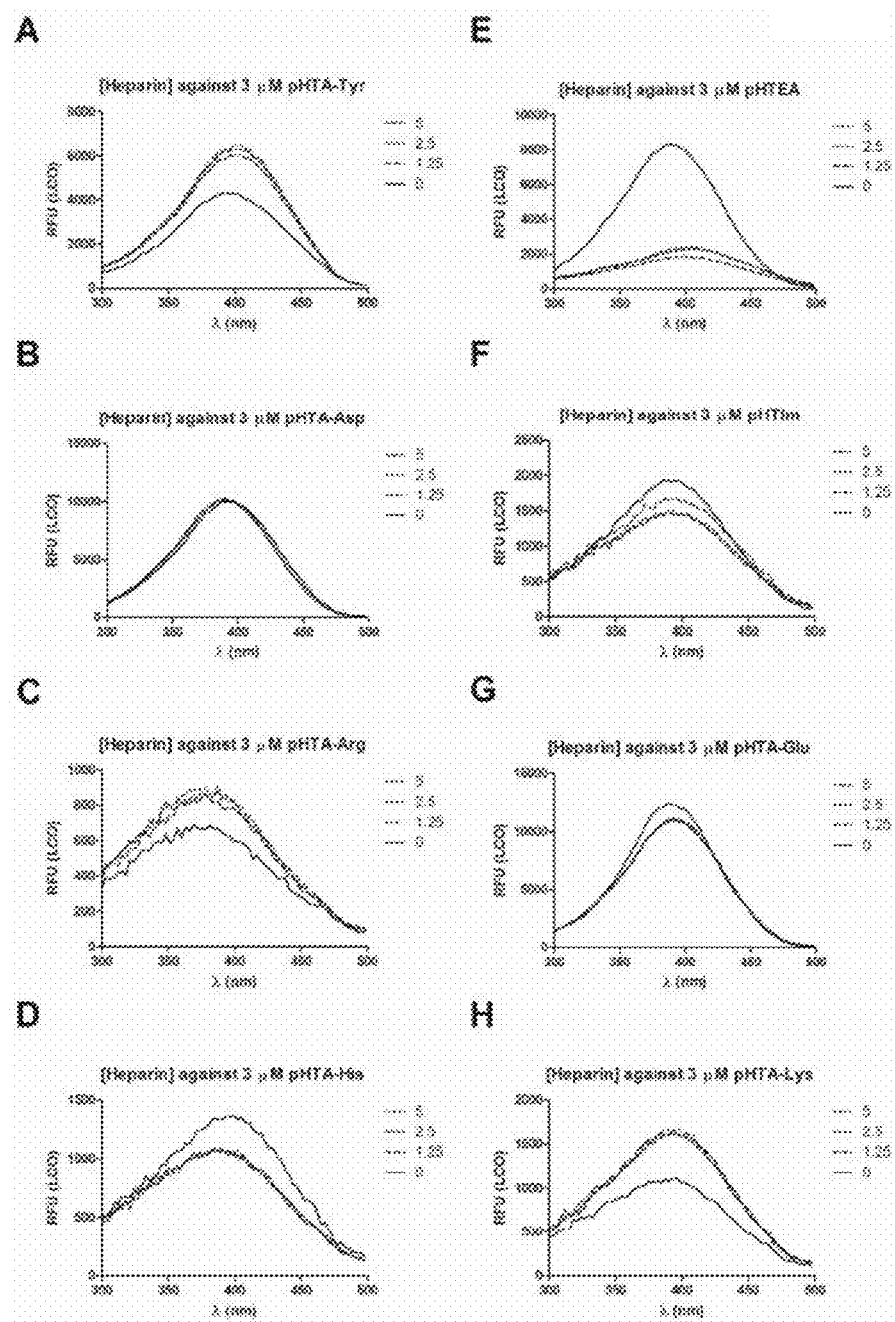
FIG. 22 shows a spectrofluorometric screen of pentameric LCOs against pure carbohydrate solutions of heparin. 3 µM of each probe was applied to serial two fold dilutions of the carbohydrate of which the concentration shown here are 5 mg/ml (_.), 2.5 mg/ml (. . . ), 1.25 mg/ml (__) and 0 mg/ml (_). The excitation spectrum of the probe was analyzed for wavelengths 300-500 nm with emission read at 545 nm. Combinations are as follows; heparin against A) pHTA-Tyr; B) pHTA-Asp; C) pHTA-Arg; D) pHTA-His; E) pHTEA; F) pHTIm; G) pHTA-Glu; and H) pHTA-Lys.
Figure 23:
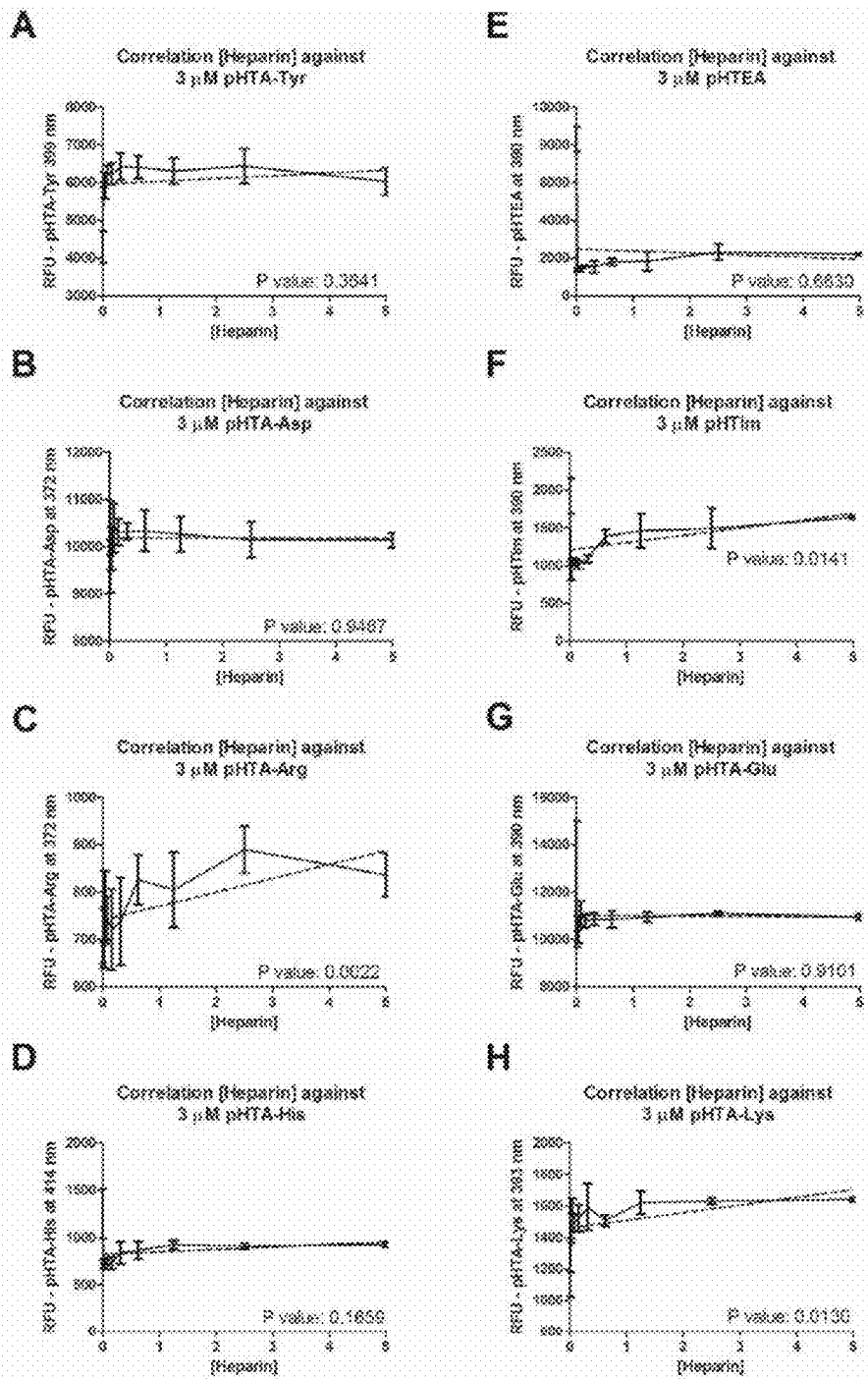
FIG. 23 shows a correlation analysis of the fluorescence intensity of pentameric LCOs against the concentration of pure carbohydrate solutions of heparin present in the assay. 3 µM of each probe was applied to serial two fold dilutions of the carbohydrate. Respective probes were excited at wavelengths unique to each probe (specified in figure), and emission was read at 545 nm. Combinations are shown as follows; heparin against A) pHTA-Tyr; B) pHTA-Asp; C) pHTA-Arg; D) pHTA-His; E) pHTEA; F) pHTIm; G) pHTA-Glu; and H) pHTA-Lys. The mean increase in signal (_) with [heparin] and the fitted regression line (__) is shown.
Figure 24:
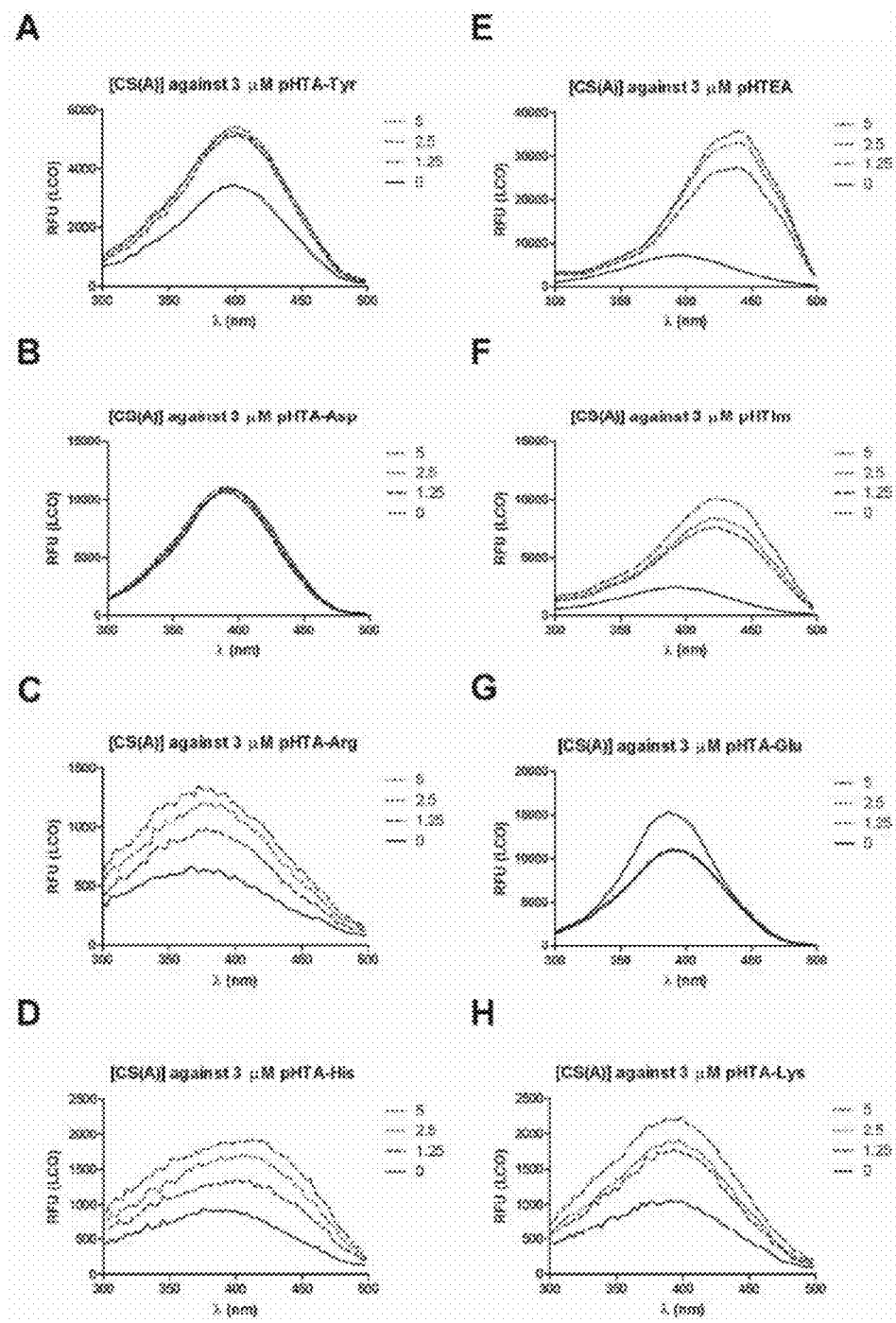
FIG. 24 shows a spectrofluorometric screen of pentameric LCOs against pure carbohydrate solutions of Chondroitin Sulfate A (CS(A)) 3 µM of each probe was applied to serial two fold dilutions of the carbohydrate of which the concentration shown here are 0.5 mg/ml (_.), 0.25 mg/ml ( . . . ) 0.125 mg/ml (__) and 0 mg/ml (_). The excitation spectrum of the probe was analyzed for wavelengths 300-500 nm with emission read at 545 nm. Combinations are as follows; CS(A) against A) pHTA-Tyr; B) pHTA-Asp; C) pHTA-Arg; D) pHTA-His; E) pHTEA; F) pHTIm; G) pHTA-Glu; and H) pHTA-Lys.
Figure 25:
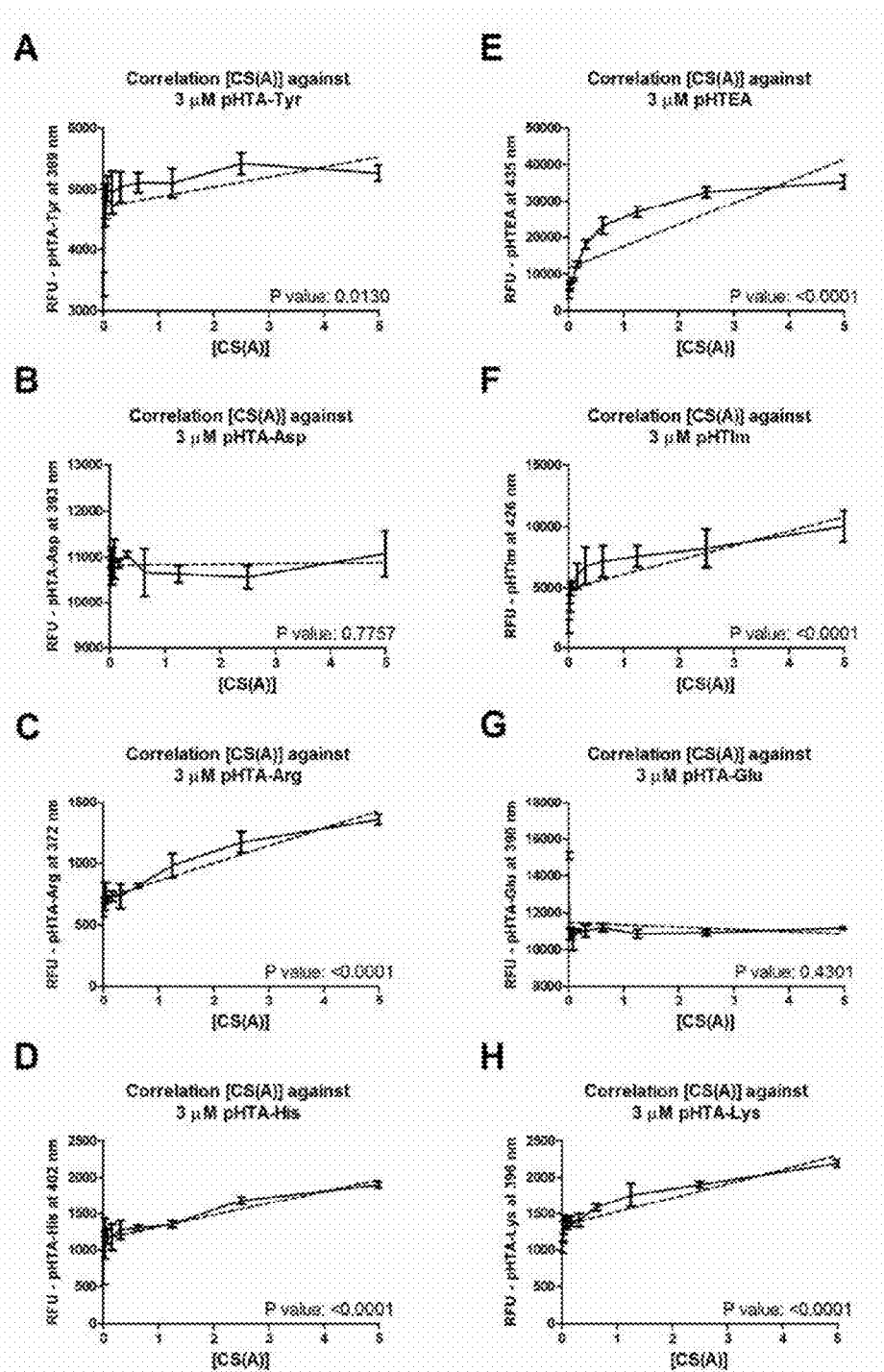
FIG. 25 shows a correlation analysis of the fluorescence intensity of pentameric LCOs against the concentration of pure carbohydrate solutions of CS(A) present in the assay. 3 µM of each probe was applied to serial two fold dilutions of the carbohydrate. Respective probes were excited at wavelengths unique to each probe (specified in figure), and emission was read at 545 nm. Combinations are shown as follows; CS(A) against A) pHTA-Tyr; B) pHTA-Asp; C) pHTA-Arg; D) pHTA-His; E) pHTEA; F) pHTIm; G) pHTA-Glu; and H) pHTA-Lys. The mean increase in signal (_) with [Chrondroitin Sulfate A] and the fitted regression line (__) is shown.

Analysis of ΔbscA (FIG. 5F) shows that in the absence of cellulose expression, curli expression no longer follows a sigmoidal trend seen in FIG. 6C. Curli production appears to increase gradually throughout. Once again, due to the wide emission spectrum of curli bound LCO, a degree of spillover is detected in the cellulose fluorescence channel.

When cellulose is not present in the ECM, as in ΔbscA (FIG. 5F), the dynamics of ECM formation is changed. In contrast to the wt (FIG. 5C) and ΔcsgA (FIG. 5E) cultures, there was no apparent 'time lag' between the exponential phase of culture growth and the induction of ECM formation. Curli production appeared to increase gradually throughout.

Conclusion:

The LCO probe h-FTAA enables real time analysis of biofilm formation. Cellulose and curli specific signals could be detected every hour in an ongoing culture. The increase in signal over time reflects increase in biofilm quantity as it is being formed. Comparison of culture growth (represented by GFP signal) and biofilm signals from the h-FTAA suggest that biofilm formation occurs when the culture reaches stationary phase, which is in agreement with previous studies. Channels selected for curli and cellulose detection do not experience significant noise from GFP fluorescence. The wide emission spectrum of curli/cellulose bound h-FTAA bleeds through into the GFP channel. However, this does not affect analysis.

Example 5—Evaluation of the Ability of LCOs to Bind and Discriminate Structural Carbohydrates (e.g. β-1,3-Glucan, Cellulose, Chitin, Sodium Alginate), Metabolic Substrates and Intermediates (e.g. α-D-Glucose, Cellulobiose), Storage Carbohydrates (e.g. Amylose, Glycogen), and Glycoaminoglycans (e.g. Heparin, Chondroitin Sulfate A)

Aim of Study:

To demonstrate the use of pentameric LCOs in differentiating β-1,3-glucan, cellulose, chitin, sodium alginate, α-D-glucose, cellulobiose, amylose, glycogen, heparin, and chondroitin sulfate A by studying changes in the excitation wavelength for maximum emission (λmax), and the correlation between signal intensity and carbohydrate concentration.

Study Design:

Serial dilutions of carbohydrate suspensions were prepared in $dH_2O$. Concentrations ranging from 10 to 0.039 mg/ml was used for β-1,3-glucan, cellulose and chitin, whereas 5 to 0.019 mg/ml was used for sodium alginate, glucose, amylose, glycogen, cellulobiose, heparin, chondroitin sulfate A. 3 μM of each LCO probe was added to 1 ml aliquots of each concentration of carbohydrate, after which 100 μl was dispensed in triplicates into 96 well plates. Excitation spectra were collected by exciting the sample from 300 to 500 nm and detecting emission at 545 nm. Detection of carbohydrate is concluded when there is a reproducible change in λmax and/or RFU intensity with reference to the negative control. Data from three concentrations, as well as the negative control are shown for each carbohydrate as specified in respective figure.

The correlation and trend between signal intensity and carbohydrate concentration was shown by plotting the concentration of the carbohydrate against the corresponding fluorescence signal of carbohydrate bound LCO. The excitation wavelength (emission detected at 545 nm) selected for each LCO is either (1) the λmax, or (2) the excitation wavelength which suffers the lowest background. A linear regression analysis is performed to determine the relationship between the carbohydrate concentration and RFU.

Results are shown in FIGS. 6-25 and are summarized in Tables 1-10 below.

TABLE 1

β-1,3-glucan (10-0.039 mg/ml)

| | | Spectral analysis (Excitation 300-500, Emission 545) | | | | | | Correlation analysis | | | | |
|---|---|---|---|---|---|---|---|---|---|---|---|---|
| | | Signal deviation with increasing [Carbohydrate] | | | | | | Gradient of regression line | | | | |
| Probe | FIG. | RFU change | λmax change | λmax-Unbound (nm) | λmax-Bound (nm) | FIG. | Excitation λ (nm) | RFU change | Deviation from null (P-Value) | Gradient Parameters | Quality of Gradient | Linear relationship | Sensitivity |
| pHTA-Tyr | 6 A | Decrease | No Change | 400 | 400 | 7 A | 402 | Decrease | 0.2754 | −53.2 ± 47.5 | Horizontal | Not Significant | No |
| pHTA-Asp | 6 B | Decrease | No Change | 393 | 393 | 7 B | 393 | Decrease | <0.0001 | −792.9 ± 97.3 | Negative | Significant | Yes |
| pHTA-Arg | 6 C | Increase | No Change | 390 | 390 | 7 C | 390 | Increase | <0.0001 | 119.1 ± 16.69 | Positive | Significant | Yes |
| pHTA-His | 6 D | Unclear | No Change | 399 | 399 | 7 D | 399 | Unclear | 0.8373 | −7.071 ± 34 | Horizontal | Not Significant | No |
| pHTEA | 6 E | Decrease | Redshift | 387 | 408 | 7 E | 405 | Decrease | 0.0039 | −664.6 ± 206.2 | Negative | Significant | Yes |

TABLE 1-continued

β-1,3-glucan (10-0.039 mg/ml)

| | | Spectral analysis (Excitation 300-500, Emission 545) | | | | Correlation analysis | | | | | | |
|---|---|---|---|---|---|---|---|---|---|---|---|---|
| | | Signal deviation with increasing [Carbohydrate] | | | | | | | Gradient of regression line | | | |
| Probe | FIG. | RFU change | λmax change | λmax-Unbound (nm) | λmax-Bound (nm) | FIG. | Excitation λ (nm) | RFU change | Deviation from null (P-Value) | Gradient Parameters | Quality of Gradient | Linear relationship | Sensitivity |
| pHTIm | 6 F | Decrease | Redshift | 391 | 402 | 7 F | 402 | Decrease | 0.2051 | −177.1 ± 89.6 | Horizontal | Not Significant | No |
| pHTA-Glu | 6 G | Decrease | No Change | 393 | 393 | 7 G | 393 | Decrease | <0.0001 | −898.7 ± 117.0 | Negative | Significant | Yes |
| pHTA-Lys | 6 H | Decrease | No Change | 399 | 399 | 7 H | 399 | Increase | <0.0001 | 107.9 ± 16.4 | Positive | Significant | Yes |

TABLE 2

Cellulose (10-0.039 mg/ml)

| | | Spectral analysis (Excitation 300-500, Emission 545) | | | | Correlation analysis | | | | | | |
|---|---|---|---|---|---|---|---|---|---|---|---|---|
| | | Signal deviation with increasing [Carbohydrate] | | | | | | | Gradient of regression line | | | |
| Probe | FIG. | RFU change | λmax change | λmax-Unbound (nm) | λmax-Bound (nm) | FIG. | Excitation λ (nm) | RFU change | Deviation from null (P-Value) | Gradient Parameters | Quality of Gradient | Linear relationship | Sensitivity |
| pHTA-Tyr | 8 A | Unclear | No Change | 399 | 399 | 9 A | 399 | Unclear | 0.2662 | −51.4 ± 45.0 | Horizontal | Not Significant | No |
| pHTA-Asp | 8 B | Unclear | No Change | 390 | 390 | 9 B | 399 | Unclear | 0.8503 | 12.3 ± 64.4 | Horizontal | Not Significant | No |
| pHTA-Arg | 8 C | Increase | Redshift | 386 | 444 | 9 C | 447 | Increase | <0.0001 | 194.0 ± 29.9 | Positive | Significant | Yes |
| pHTA-His | 8 D | Increase | Redshift | 399 | 444 | 9 D | 444 | Increase | <0.0001 | 725.9 ± 124.6 | Positive | Significant | Yes |
| pHTEA | 8 E | Increase | Redshift | 386 | 444 | 9 E | 444 | Increase | <0.0001 | 6001 ± 1187 | Positive | Significant | Yes |
| pHTIm | 8 F | Increase | Redshift | 390 | 444 | 9 F | 444 | Increase | <0.0001 | 3063 ± 564.3 | Positive | Significant | Yes |
| pHTA-Glu | 8 G | Unclear | No Change | 396 | 396 | 9 G | 396 | Decrease | 0.6893 | −139.6 ± 344.8 | Horizontal | Not Significant | No |
| pHTA-Lys | 8 H | Increase | Redshift | 398 | 441 | 9 H | 396 | Increase | <0.0001 | 291.8 ± 46.6 | Positive | Significant | Yes |

TABLE 3

Chitin (10-0.039 mg/ml)

| | | Spectral analysis (Excitation 300-500, Emission 545) | | | | Correlation analysis | | | | | | |
|---|---|---|---|---|---|---|---|---|---|---|---|---|
| | | Signal deviation with increasing [Carbohydrate] | | | | | | | Gradient of regression line | | | |
| Probe | FIG. | RFU change | λmax change | λmax-Unbound (nm) | λmax-Bound (nm) | FIG. | Excitation λ (nm) | RFU change | Deviation from null (P-Value) | Gradient Parameters | Quality of Gradient | Linear relationship | Sensitivity |
| pHTA-Tyr | 10 A | Increases | Redshift | 404 | 411 | 11 A | 441 | Increases | <0.0001 | 972.3 ± 109.7 | Positive | Significant | Yes |
| pHTA-Asp | 10 B | Increases | Redshift | 392 | 443 | 11 B | 441 | Increases | <0.0001 | 3138 ± 491.2 | Positive | Significant | Yes |
| pHTA-Arg | 10 C | Increases | Redshift | 387 | 417 | 11 C | 417 | Increases | <0.0001 | 338.2 ± 19.4 | Positive | Significant | Yes |
| pHTA-His | 10 D | Increases | Redshift | 399 | 412 | 11 D | 411 | Increases | 0.0002 | 117.2 ± 25.7 | Positive | Significant | Yes |
| pHTEA | 10 E | Decrease | Redshift | 387 | 397 | 11 E | 396 | Decreases | <0.0001 | −9030 ± 110.1 | Negative | Significant | Yes |
| pHTIm | 10 F | Decrease | Redshift | 390 | 400 | 11 F | 399 | Decreases | <0.0001 | −383.6 ± 71.4 | Negative | Significant | Yes |

TABLE 3-continued

Chitin (10-0.039 mg/ml)

| | | Spectral analysis (Excitation 300-500, Emission 545) | | | | | | | | | | |
|---|---|---|---|---|---|---|---|---|---|---|---|---|
| | | Signal deviation with increasing [Carbohydrate] | | | | Correlation analysis | | | | | | |
| | | | | | | | | | Gradient of regression line | | | |
| Probe | FIG. | RFU change | λmax change | λmax-Unbound (nm) | λmax-Bound (nm) | FIG. | Excitation λ (nm) | RFU change | Deviation from null (P-Value) | Gradient Parameters | Quality of Gradient | Linear relationship | Sensitivity |
| pHTA-Glu | 10 G | Increases | Redshift | 396 | 435 | 11 G | 435 | Increases | <0.0001 | 2824 ± 156.6 | Positive | Significant | Yes |
| pHTA-Lys | 10 H | Increases | Redshift | 397 | 437 | 11 H | 435 | Increases | <0.0001 | 273.8 ± 46.2 | Positive | Significant | Yes |

TABLE 4

Sodium alginate (5-0.019 mg/ml)

| | | Spectral analysis (Excitation 300-500, Emission 545) | | | | | | | | | | |
|---|---|---|---|---|---|---|---|---|---|---|---|---|
| | | Signal deviation with increasing [Carbohydrate] | | | | Correlation analysis | | | | | | |
| | | | | | | | | | Gradient of regression line | | | |
| Probe | FIG. | RFU change | λmax change | λmax-Unbound (nm) | λmax-Bound (nm) | FIG. | Excitation λ (nm) | RFU change | Deviation from null (P-Value) | Gradient Parameters | Quality of Gradient | Linear relationship | Sensitivity |
| pHTA-Tyr | 12 A | Increases | No Change | 402 | 403 | 13 A | 402 | Unclear | 0.8611 | 30.9 ± 175.5 | Horizontal | Not Significant | No |
| pHTA-Asp | 12 B | Unclear | No Change | 390 | 390 | 13 B | 390 | Unclear | 0.4928 | 41.4 ± 59.6 | Horizontal | Not Significant | No |
| pHTA-Arg | 12 C | Increases | No Change | 375 | 375 | 13 C | 375 | Increases | 0.0002 | 78.6 ± 18.6 | Positive | Significant | Yes |
| pHTA-His | 12 D | Increases | No Change | 396 | 396 | 13 D | 414 | Increases | <0.0001 | 199.9 ± 36.3 | Positive | Significant | Yes |
| pHTEA | 12 E | Increases | Redshift | 396 | 409 | 13 E | 405 | Increases | <0.0001 | 832.4 ± 174.5 | Positive | Significant | Yes |
| pHTIm | 12 F | Increases | Redshift | 399 | 409 | 13 F | 381 | Increases | <0.0001 | 266 ± 29.2 | Positive | Significant | Yes |
| pHTA-Glu | 12 G | Increases | No Change | 391 | 391 | 13 G | 390 | Increases | 0.1636 | 88.7 ± 62.0 | Horizontal | Not Significant | No |
| pHTA-Lys | 12 H | Increases | No Change | 390 | 390 | 13 H | 396 | Increases | <0.0001 | 55.4 ± 5.3 | Positive | Significant | Yes |

TABLE 5

Glucose (5-0.019 mg/ml)

| | | Spectral analysis (Excitation 300-500, Emission 545) | | | | | | | | | | |
|---|---|---|---|---|---|---|---|---|---|---|---|---|
| | | Signal deviation with increasing [Carbohydrate] | | | | Correlation analysis | | | | | | |
| | | | | | | | | | Gradient of regression line | | | |
| Probe | FIG. | RFU change | λmax change | λmax-Unbound (nm) | λmax-Bound (nm) | FIG. | Excitation λ (nm) | RFU change | Deviation from null (P-Value) | Gradient Parameters | Quality of Gradient | Linear relationship | Sensitivity |
| pHTA-Tyr | 14 A | Increases | No Change | 402 | 402 | 15 A | 402 | Increases | <0.0001 | 799.4 ± 95.1 | Positive | Significant | Yes |
| pHTA-Asp | 14 B | Increases | No Change | 390 | 390 | 15 B | 393 | Increases | <0.0001 | 625.1 ± 130.2 | Positive | Significant | Yes |
| pHTA-Arg | 14 C | Increases | No Change | 387 | 387 | 15 C | 393 | Unclear | 0.6419 | 17.9 ± 38.1 | Horizontal | Not Significant | No |
| pHTA-His | 14 D | Increases | No Change | 399 | 399 | 15 D | 390 | Unclear | 0.198 | 33.2 ± 25.2 | Horizontal | Not Significant | No |
| pHTEA | 14 E | Increases | No Change | 387 | 387 | 15 E | 399 | Unclear | 0.0807 | −67.4 ± 37.2 | Horizontal | Not Significant | No |

TABLE 5-continued

Glucose (5-0.019 mg/ml)

| | | Spectral analysis (Excitation 300-500, Emission 545) | | | | | | | | | | |
|---|---|---|---|---|---|---|---|---|---|---|---|---|
| | | Signal deviation with increasing [Carbohydrate] | | | | Correlation analysis | | | | | | |
| | | | | | | | | | Gradient of regression line | | | |
| Probe | FIG. | RFU change | λmax change | λmax-Unbound (nm) | λmax-Bound (nm) | FIG. | Excitation λ (nm) | RFU change | Deviation from null (P-Value) | Gradient Parameters | Quality of Gradient | Linear relationship | Sensitivity |
| pHTIm | 14 F | Unclear | No Change | 390 | 390 | 15 F | 387 | Unclear | 0.6705 | 10.9 ± 25.5 | Horizontal | Not Significant | No |
| pHTA-Glu | 14 G | Decreases | No Change | 390 | 390 | 15 G | 396 | Decreases | 0.0085 | −116.0 ± 41.0 | Negative | Significant | Yes |
| pHTA-Lys | 14 H | Unclear | No Change | 399 | 399 | 15 H | 396 | Unclear | 0.0957 | 23.6 ± 13.7 | Horizontal | Not Significant | No |

TABLE 6

Amylose (5-0.019 mg/ml)

| | | Spectral analysis (Excitation 300-500, Emission 545) | | | | | | | | | | |
|---|---|---|---|---|---|---|---|---|---|---|---|---|
| | | Signal deviation with increasing [Carbohydrate] | | | | Correlation analysis | | | | | | |
| | | | | | | | | | Gradient of regression line | | | |
| Probe | FIG. | RFU change | λmax change | λmax-Unbound (nm) | λmax-Bound (nm) | FIG. | Excitation λ (nm) | RFU change | Deviation from null (P-Value) | Gradient Parameters | Quality of Gradient | Linear relationship | Sensitivity |
| pHTA-Tyr | 16 A | Unclear | No Change | 402 | 402 | 17 A | 402 | Unclear | 0.3091 | −133.1 ± 128.5 | Horizontal | Not Significant | No |
| pHTA-Asp | 16 B | Increases | No Change | 390 | 390 | 17 B | 390 | Increases | 0.9699 | −7.6 ± 208.9 | Horizontal | Not Significant | Yes |
| pHTA-Arg | 16 C | Unclear | No Change | 386 | 386 | 17 C | 387 | Unclear | 0.1997 | −28.4 ± 21.6 | Horizontal | Not Significant | No |
| pHTA-His | 16 D | Decreases | Blue-shift | 401 | 385 | 17 D | 402 | Decreases | <0.0001 | −341.5 ± 47.3 | Negative | Significant | Yes |
| pHTEA | 16 E | Decreases | No Change | 388 | 388 | 17 E | 387 | Decreases | <0.0001 | −6680 ± 1421 | Negative | Significant | Yes |
| pHTIm | 16 F | Decreases | Blue-shift | 392 | 382 | 17 F | 396 | Decreases | <0.0001 | −655 ± 110 | Negative | Significant | Yes |
| pHTA-Glu | 16 G | Increases | Blue-shift | 395 | 390 | 17 G | 393 | Increases | 0.1659 | 493.6 ± 346.9 | Horizontal | Not Significant | Yes |
| pHTA-Lys | 16 H | Increases | No Change | 395 | 395 | 17 H | 396 | Increases | 0.0158 | 47.7 ± 18.5 | Positive | Significant | Yes |

TABLE 7

Glycogen (5-0.019 mg/ml)

| | | Spectral analysis (Excitation 300-500, Emission 545) | | | | | | | | | | |
|---|---|---|---|---|---|---|---|---|---|---|---|---|
| | | Signal deviation with increasing [Carbohydrate] | | | | Correlation analysis | | | | | | |
| | | | | | | | | | Gradient of regression line | | | |
| Probe | FIG. | RFU change | λmax change | λmax-Unbound (nm) | λmax-Bound (nm) | FIG. | Excitation λ (nm) | RFU change | Deviation from null (P-Value) | Gradient Parameters | Quality of Gradient | Linear relationship | Sensitivity |
| pHTA-Tyr | 18 A | Decreases | Redshift | 401 | 405 | 19 A | 402 | Decreases | <0.0001 | −2062 ± 216.6 | Negative | Significant | Yes |
| pHTA-Asp | 18 B | Decreases | Redshift | 391 | 400 | 19 B | 393 | Decreases | <0.0001 | −665.8 ± 88.9 | Negative | Significant | Yes |
| pHTA-Arg | 18 C | Increases | Redshift | 376 | 391 | 19 C | 391 | Increases | <0.0001 | 72.8 ± 13.4 | Positive | Significant | Yes |
| pHTA-His | 18 D | Increases | Redshift | 393 | 414 | 19 D | 402 | Increases | 0.0262 | 130.6 ± 55.6 | Positive | Significant | Yes |

TABLE 7-continued

Glycogen (5-0.019 mg/ml)

Spectral analysis
(Excitation 300-500, Emission 545)

| Probe | FIG. | Signal deviation with increasing [Carbohydrate] | | λmax-Unbound (nm) | λmax-Bound (nm) | Correlation analysis | | | | | | Sensitivity |
|---|---|---|---|---|---|---|---|---|---|---|---|---|
| | | RFU change | λmax change | | | FIG. | Excitation λ (nm) | RFU change | Deviation from null (P-Value) | Gradient Parameters | Quality of Gradient | Linear relationship |
| pHTEA | 18 E | Decreases | Redshift | 389 | 411 | 19 E | 390 | Decreases | 0.1804 | −451 ± 328 | Negative | Not Significant | Yes |
| pHTIm | 18 F | Increases | Redshift | 389 | 411 | 19 F | 408 | Increases | <0.0001 | 835.8 ± 26.6 | Positive | Significant | Yes |
| pHTA-Glu | 18 G | Decreases | Redshift | 390 | 403 | 19 G | 396 | Decreases | 0.0012 | −349.2 ± 96.7 | Negative | Significant | Yes |
| pHTA-Lys | 18 H | Increases | Blueshift | 390 | 384 | 19 H | 399 | Increases | <0.0001 | 43.6 ± 7.9 | Positive | Significant | Yes |

TABLE 8

Cellulobiose (5-0.019 mg/ml)

Spectral analysis
(Excitation 300-500, Emission 545)

| Probe | FIG. | Signal deviation with increasing [Carbohydrate] | | λmax-Unbound (nm) | λmax-Bound (nm) | Correlation analysis | | | | | | Sensitivity |
|---|---|---|---|---|---|---|---|---|---|---|---|---|
| | | RFU change | λmax change | | | FIG. | Excitation λ (nm) | RFU change | Deviation from null (P-Value) | Gradient Parameters | Quality of Gradient | Linear relationship |
| pHTA-Tyr | 20 A | Increases | No change | 402 | 402 | 21 A | 402 | Increases | 0.0015 | 56.7 ± 16 | Positive | Significant | Yes |
| pHTA-Asp | 20 B | Increases | No change | 402 | 402 | 21 B | 402 | Increases | 0.0278 | 91.2 ± 39.3 | Positive | Significant | Yes |
| pHTA-Arg | 20 C | Unclear | No change | 360 | 360 | 21 C | 360 | Unclear | 0.9204 | −1.30 ± 12.9 | Horizontal | Not Significant | No |
| pHTA-His | 20 D | Unclear | No change | 357 | 357 | 21 D | 357 | Unclear | 0.2898 | −5.26 ± 4.87 | Horizontal | Not Significant | No |
| pHTEA | 20 E | Unclear | No change | 387 | 387 | 21 E | 387 | Unclear | 0.5571 | 39.5 ± 66.5 | Horizontal | Not Significant | No |
| pHTIm | 20 F | Increases | No change | 390 | 390 | 21 F | 390 | Unclear | 0.2321 | 75.1 ± 61.5 | Horizontal | Not Significant | No |
| pHTA-Glu | 20 G | Increases | No change | 393 | 393 | 21 G | 393 | Increases | <0.0001 | 178.6 ± 35.1 | Positive | Significant | Yes |
| pHTA-Lys | 20 H | Unclear | No change | 369 | 369 | 21 H | 369 | Unclear | 0.1125 | 6.45 ± 3.93 | Horizontal | Not Significant | No |

TABLE 9

Heparin (5-0.019 mg/ml)

Spectral analysis
(Excitation 300-500, Emission 545)

| Probe | FIG. | Signal deviation with increasing [Carbohydrate] | | λmax-Unbound (nm) | λmax-Bound (nm) | Correlation analysis | | | | | | Sensitivity |
|---|---|---|---|---|---|---|---|---|---|---|---|---|
| | | RFU change | λmax change | | | FIG. | Excitation λ (nm) | RFU change | Deviation from null (P-Value) | Gradient Parameters | Quality of Gradient | Linear relationship |
| pHTA-Tyr | 22 A | Increases | No change | 399 | 399 | 23 A | 399 | Increases | 0.3641 | 74.5 ± 80.7 | Horizontal | Not Significant | No |
| pHTA-Asp | 22 B | Unclear | No change | 390 | 390 | 23 B | 372 | Unclear | 0.9487 | −3.2 ± 49.3 | Horizontal | Not Significant | No |
| pHTA-Arg | 22 C | Increases | No change | 374 | 374 | 23 C | 372 | Increases | 0.0022 | 29.3 ± 8.6 | Positive | Significant | Yes |

TABLE 9-continued

Heparin (5-0.019 mg/ml)

Spectral analysis (Excitation 300-500, Emission 545)

| Probe | FIG. | Signal deviation with increasing [Carbohydrate] | | | | Correlation analysis | | | | | | |
|---|---|---|---|---|---|---|---|---|---|---|---|---|
| | | RFU change | λmax change | λmax-Unbound (nm) | λmax-Bound (nm) | FIG. | Excitation λ (nm) | RFU change | Deviation from null (P-Value) | Gradient Parameters | Quality of Gradient | Linear relationship | Sensitivity |
| pHTA-His | 22 D | Decreases | No change | 414 | 414 | 23 D | 414 | Unclear | 0.1659 | 26.3 ± 18.5 | Horizontal | Not Significant | No |
| pHTEA | 22 E | Decreases | Redshift | 395 | 403 | 23 E | 390 | Unclear | 0.663 | −109.3 ± 248 | Horizontal | Not Significant | No |
| pHTIm | 22 F | Unclear | No change | 392 | 392 | 23 F | 390 | Increases | 0.0141 | 96.3 ± 36.8 | Positive | Significant | Yes |
| pHTA-Glu | 22 G | Unclear | No change | 390 | 390 | 23 G | 390 | Unclear | 0.9101 | −12.4 ± 108 | Horizontal | Not Significant | No |
| pHTA-Lys | 22 H | Increases | No change | 393 | 393 | 23 H | 393 | Increases | 0.013 | 48.4 ± 18.2 | Positive | Significant | Yes |

TABLE 10

Chondroitin Sulfate A (5-0.019 mg/ml)

Spectral analysis (Excitation 300-500, Emission 545)

| Probe | FIG. | Signal deviation with increasing [Carbohydrate] | | | | Correlation analysis | | | Gradient of regression line | | | |
|---|---|---|---|---|---|---|---|---|---|---|---|---|
| | | RFU change | λmax change | λmax-Unbound (nm) | λmax-Bound (nm) | FIG. | Excitation λ (nm) | RFU change | Deviation from null (P-Value) | Gradient Parameters | Quality of Gradient | Linear relationship | Sensitivity |
| pHTA-Tyr | 24 A | Increases | No change | 399 | 399 | 25 A | 399 | Increases | 0.013 | 163.3 ± 61.5 | Positive | Significant | Yes |
| pHTA-Asp | 24 B | Unclear | No change | 390 | 390 | 25 B | 393 | Unclear | 0.7757 | −67.88 ± 90.0 | Horizontal | Not Significant | No |
| pHTA-Arg | 24 C | Increases | No change | 372 | 372 | 25 C | 372 | Increases | <0.0001 | 143.4 ± 10.01 | Positive | Significant | Yes |
| pHTA-His | 24 D | Increases | Blueshift | 402 | 390 | 25 D | 402 | Increases | <0.0001 | 163.8 ± 20.77 | Positive | Significant | Yes |
| pHTEA | 24 E | Increases | Redshift | 408 | 438 | 25 E | 435 | Increases | <0.0001 | 5989 ± 727 | Positive | Significant | Yes |
| pHTIm | 24 F | Increases | Redshift | 408 | 424 | 25 F | 426 | Increases | <0.0001 | 1177 ± 203.6 | Positive | Significant | Yes |
| pHTA-Glu | 24 G | Decreases | No change | 391 | 391 | 25 G | 390 | Unclear | 0.4301 | 125.3 ± 156.5 | Horizontal | Not Significant | No |
| pHTA-Lys | 24 H | Decreases | No change | 395 | 395 | 25 H | 396 | Increases | <0.0001 | 194.8 ± 19.2 | Positive | Significant | Yes |

Conclusion:

Based on a change (positive or negative) in magnitude of detected signal and/or a shift in λmax upon binding of the LCO to the carbohydrate, conclusions are drawn that the carbohydrates can be detected and/or differentiated by specific LCOs as indicated below:

β-1,3-Glucan pHTA-Asp, pHTA-Arg, pHTEA, pHTA-Glu, pHTA-Lys
Cellulose pHTA-Arg, pHTA-His, pHTEA, pHTIm, pHTA-Lys
Chitin pHTA-Tyr, pHTA-Asp, pHTA-Arg, pHTA-His, pHTEA, pHTIm. pHTA-Glu, pHTA-Lys
Sodium alginate pHTA-Arg, pHTA-His, pHTEA, pHTIm, pHTA-Lys
Glucose pHTA-Tyr, pHTA-Asp, pHTA-Glu
Amylose pHTA-Asp, pHTA-His, pHTEA, pHTIm, pHTA-Glu, pHTA-Lys
Glycogen pHTA-Tyr, pHTA-Asp, pHTA-Arg, pHTA-His, pHTEA, pHTIm pHTA-Glu, pHTA-Lys
Cellobiose pHTA-Tyr, pHTA-Asp, pHTA-Glu
Heparin pHTA-Arg, pHTIm, pHTA-Glu
Chondroitin sulfate A: pHTA-Tyr, pHTA-Arg, pHTA-His. pHTEA, pHTIm, pHTA-Lys

The invention claimed is:

1. A method for detection, identification and/or quantification of one or more carbohydrates, comprising the steps of:
   a) contacting an object or a sample with a pentameric to 15-meric luminescent conjugated oligothiophene;
   b) detecting at least one detection signal of the luminescent conjugated oligothiophene; and
   c) based on said detected detection signal determining the presence, identity and/or quantity of the carbohydrate or carbohydrates on said object or in said sample.

2. The method according to claim 1, wherein said luminescent conjugated oligothiophene is a pentameric or heptameric luminescent conjugated oligothiophene.

3. The method according to claim 1, wherein said luminescent conjugated oligothiophene comprises one or more functional side chains.

4. The method according to claim 3, wherein said functional side chain(s) is/are selected from amino acids, neurotransmitters, monosaccharides, polysaccharides, nucleic acids and combinations thereof.

5. The method according to claim 2, wherein said heptameric luminescent conjugated oligothiophene is heptamer formyl thiophene acetic acid (h-FTAA) or heptamer hydrogen thiophene acetic acid (h-HTAA), and said pentameric luminescent conjugated oligothiophene is any of pentamer hydrogen thiophene acetic acid histidine (pHTA-His), pentamer hydrogen thiophene acetic acid lysine (pHTA-Lys), pentamer hydrogen thiophene ethanol amine (pHTEA), pentamer hydrogen thiophene imidazole (pHTIm), pentamer hydrogen thiophene acetic acid tyrosine (pHTA-Tyr), pentamer hydrogen thiophene acetic acid arginine (pHTA-Arg), pentamer hydrogen thiophene acetic acid aspartate (pHTA-Asp), and pentamer hydrogen thiophene acetic acid glutamate (pHTA-Glu).

6. The method according to claim 1, wherein said detection signal is an optical signal.

7. The method according to claim 1, wherein the luminescent conjugated oligothiophene is able to discriminate between at least two different carbohydrates.

8. The method according to claim 1, wherein at least one of the carbohydrates is an insoluble carbohydrate.

9. The method according to claim 8, wherein said insoluble carbohydrate is any of cellulose, chitin, β-glucan, alginate, amylose and glycogen, or combinations thereof.

10. The method according to claim 1, wherein at least one of the carbohydrates is a soluble carbohydrate.

11. The method according to claim 10, wherein said soluble carbohydrate is any of glucose, cellulobiose, heparin, chondroitin sulfate A, or combinations thereof.

12. The method according to claim 1, wherein at least one of the carbohydrates is a structural carbohydrate, a storage carbohydrate, a glycoaminoglycan, an intermediate product of carbohydrate conversion and/or a metabolic substrate.

13. The method according to claim 1, wherein at least step a) and/or step b) is or are carried out in vivo, in vitro or in situ.

14. The method according to claim 6, wherein the optical signal is a fluorescence signal, a colorimetric signal, or an electrical signal.

15. The method according to claim 14, wherein the electrical signal is conductivity.

16. The method according to claim 10, wherein the sample is a tissue or blood sample.

17. The method according to claim 10, wherein the sample is a water sample.

18. The method according to claim 8, wherein the sample is from a carbohydrate manufacturing or carbohydrate extraction process.

* * * * *